United States Patent
Erion et al.

(10) Patent No.: US 10,420,781 B2
(45) Date of Patent: Sep. 24, 2019

(54) THYROID HORMONE RECEPTOR AGONIST AND USE THEREOF

(71) Applicant: Metabasis Therapeutics, Inc., San Diego, CA (US)

(72) Inventors: Mark Erion, Mountainside, NJ (US); Hongjian Jiang, Shanghai (CN); Serge Henri Boyer, San Diego, CA (US)

(73) Assignee: Metabasis Therapeutics Inc., San Diego, CA (US)

( * ) Notice: Subject to any disclaimer, the term of this patent is extended or adjusted under 35 U.S.C. 154(b) by 0 days.

(21) Appl. No.: 16/058,778

(22) Filed: Aug. 8, 2018

(65) Prior Publication Data

US 2018/0344752 A1    Dec. 6, 2018

Related U.S. Application Data

(62) Division of application No. 15/492,398, filed on Apr. 20, 2017, now abandoned.

(60) Provisional application No. 62/326,392, filed on Apr. 22, 2016.

(51) Int. Cl.
| | |
|---|---|
| *C07F 9/09* | (2006.01) |
| *C07F 9/40* | (2006.01) |
| *A61K 31/661* | (2006.01) |
| *A61K 45/06* | (2006.01) |

(52) U.S. Cl.
CPC ............ *A61K 31/661* (2013.01); *A61K 45/06* (2013.01); *C07F 9/09* (2013.01); *C07F 9/092* (2013.01); *C07F 9/40* (2013.01); *C07F 9/4006* (2013.01)

(58) Field of Classification Search
None
See application file for complete search history.

(56) References Cited

U.S. PATENT DOCUMENTS 7,514,419 B2    4/2009 Erion et al.

FOREIGN PATENT DOCUMENTS

| WO | WO 2005/051298 A2 | 6/2005 |
| WO | WO 2005/092316 A1 | 10/2005 |
| WO | WO 2006/128056 A2 | 11/2006 |
| WO | WO 2011/038207 A1 | 3/2011 |

OTHER PUBLICATIONS

Search Report in International application No. PCT/US2017/028518, dated Jun. 1, 2017.

*Primary Examiner* — Samantha L Shterengarts
(74) *Attorney, Agent, or Firm* — Knobbe, Martens, Olson & Bear LLP

(57) ABSTRACT

A thyroid hormone receptor agonist and its use in the treatment of a disease associated thyroid hormone receptor beta are described. The compound can be effective in lowering cholesterol with minimum or no adverse effects on the heart or thyroid hormone axis.

6 Claims, 9 Drawing Sheets

THYROID HORMONE RECEPTOR AGONIST AND USE THEREOF

INCORPORATION BY REFERENCE TO ANY PRIORITY APPLICATIONS

This application is a divisional of U.S. application Ser. No. 15/492,398, filed Apr. 20, 2017, which claims the benefit of U.S. Provisional Application No. 62/326,392, entitled Thyroid Hormone Receptor Agonist and Use Thereof, filed Apr. 22, 2016, the disclosure of which are incorporated herein by reference in their entirety.

BACKGROUND

Field

The instant invention relates to a thyroid hormone analog and its use for treating metabolic diseases such as obesity, NASH, hypercholesterolemia and hyperlipidemia with low adverse effects.

Description of the Related Art

The thyroid hormones (THs) play a critical role in growth, development, metabolism, and homeostasis. They are produced by the thyroid gland as thyroxine (T4) and 3,5,3'-triiodo-L-thyronine (T3). T4 is the major secreted form in humans and is enzymatically deiodinated by deiodinases to the more active form, T3, in peripheral tissues. THs exert their action by interacting with thyroid hormone receptors (TRs), which belong to the nuclear hormone receptor superfamily, and regulate the transcription of target genes.

TRs are expressed in most tissues and exist as two isoforms (TRα and TRβ). Tissue distribution studies, mouse knockout studies, and evaluation of patients with resistance to thyroid hormone (RTH) syndrome have established that TRα is the predominant isoform in the heart and regulates most cardiac functions, while the TRβ isoform predominates in the liver and the pituitary and regulates cholesterol metabolism and thyroid stimulating hormone (TSH) production, respectively. In recognition of the potential benefits associated with modulation of TRs, numerous approaches have been pursued to identify a suitable TR agonist to lower plasma cholesterol levels. However, these benefits were offset by deleterious cardiovascular side effects (tachycardia, arrhythmia) as well as effects on the thyroid hormone axis, muscle metabolism and bone loss.

SUMMARY

Some embodiments provide a compound having a structure:

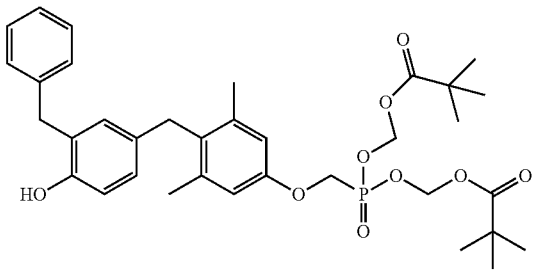 [SMILES: Cc1cc(OCP(=O)(OCOC(=O)C(C)(C)C)OCOC(=O)C(C)(C)C)cc(C)c1Cc1ccc(O)c(Cc2ccccc2)c1]

or a pharmaceutically acceptable salt thereof.

Other embodiments provide a method for the treatment of a disease that is associated with thyroid hormone receptor β, comprising administering an effective amount of the compound to a subject in need thereof.

Still other embodiments provide a method of agonizing thyroid hormone receptor β, comprising contacting the thyroid hormone receptor β with an effective amount of the compound to a subject in need thereof.

DETAILED DESCRIPTION OF THE PREFERRED EMBODIMENT

Figure 1:
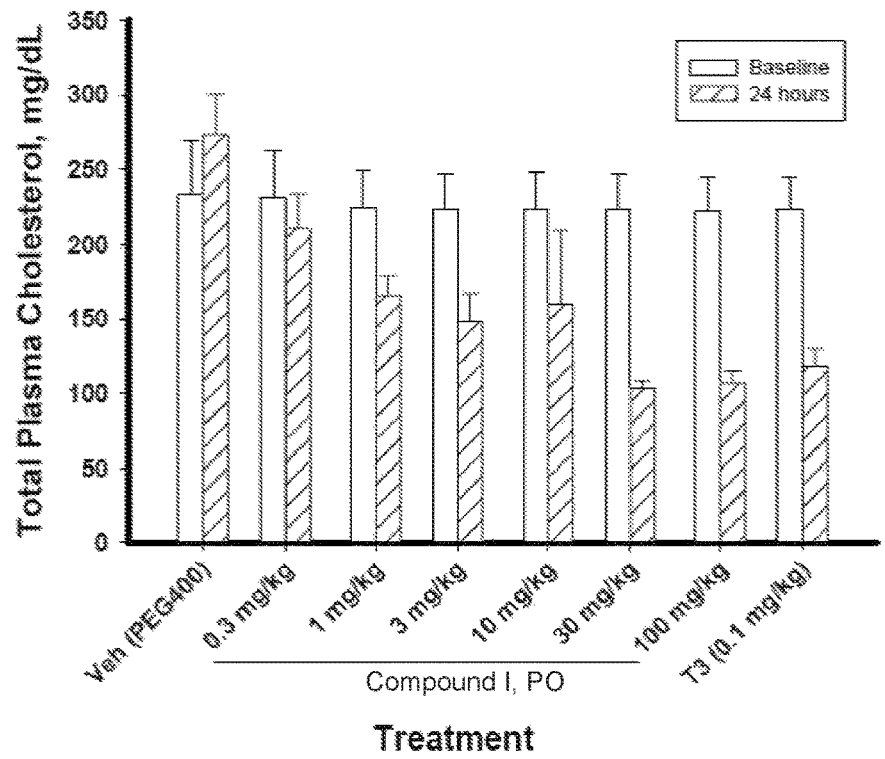
FIG. 1 shows the total plasma cholesterol levels (mean±SEM) in male, cholesterol-fed Sprague Dawley rats (n=6/group) at baseline and at 24 hours after administration of vehicle or Compound I.

Some embodiments relate to compound 1 or a pharmaceutically acceptable salt thereof.

Compound I

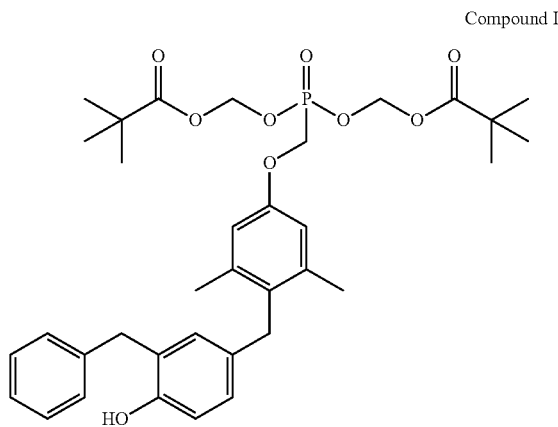 [SMILES: Cc1cc(OCP(=O)(OCOC(=O)C(C)(C)C)OCOC(=O)C(C)(C)C)cc(C)c1Cc1ccc(O)c(Cc2ccccc2)c1]

Compound I may exist in one or more crystalline or amorphous forms. Unless otherwise indicated, all such forms are included in the scope of Compound I, including any polymorphic forms. In addition, Compound I may form solvates with water (i.e., hydrates) or common organic solvents. Unless otherwise indicated, such solvates are included in the scope of Compound I.

Isotopes may be present in Compound I. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Some embodiments relate to a method of treating metabolic diseases such as obesity, NASH, hypercholesterolemia and hyperlipidemia with low adverse effects, comprising administering an effective amount of Compound I or a pharmaceutically acceptable salt thereof to a subject in need thereof.

Many previously studied thyroid hormone receptor agonists have been reported to show deleterious cardiovascular side effects (tachycardia, arrhythmia) as well as effects on the thyroid hormone axis. Erion, M. D., *Proc Natl Acad Sci*, (2007) vol 104 (39) p. 15490-15495. One leading thyroid hormone receptor agonist, (2R,4S)-4-(3-chlorophenyl)-2-[(3,5-dimethyl-4-(4'-hydroxy-3'-isopropylbenzyl)phenoxy)methyl]-2-oxido-[1,3,2]-dioxaphosphonane (MB07811), has been reported to be effective in reducing the cholesterol level and also show reduced effects on the cardiac function. Erion, M. D., *Proc Natl Acad Sci*, (2007) vol 104 (39) p. 15490-15495. However, MB07811 still shows significant effects on the thyroid hormone axis.

It has been discovered that Compound I described herein not only is effective in lowering the cholesterol, triglyceride, and lipid levels in a subject but also has minimum or no adverse cardiovascular effects (tachycardia, arrhythmia) and adverse effects on the thyroid hormone axis. Compound I also has a short active plasma half-life and rapid clearance. In addition, Compound I has shown selective activation of TRβ and minimum or no effects on T3, T4, and thyroid-stimulating hormone (TSH). Therefore, Compound I has an increased therapeutic index (TI) and surprisingly better safety profile than MB07811.

Definitions

The term "agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances.

The term "mammal" is used in its usual biological sense. Thus, it specifically includes humans, cattle, horses, dogs, cats, rats and mice but also includes many other species.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

The term "pharmaceutically acceptable salt" refers to salts that retain the biological effectiveness and properties of the compounds with which they are associated and, which are not biologically or otherwise undesirable. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

"Solvate" refers to the compound formed by the interaction of a solvent and a compound described herein, or salt thereof. Suitable solvates are pharmaceutically acceptable solvates including hydrates.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

A therapeutic effect relieves, to some extent, one or more of the symptoms of a disease or disorder, and includes curing the disease or disorder. "Curing" means that the symptoms of active disease are eliminated. However, certain long-term or permanent effects of the disease may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a patient who does not yet have the relevant disease or disorder, but who is susceptible to, or otherwise at risk of, a particular disease or disorder, whereby the treatment reduces the likelihood that the patient will develop the disease or disorder. The term "therapeutic treatment" refers to administering treatment to a patient already having a disease or disorder.

Administration and Pharmaceutical Compositions

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated herein by reference in its entirety. Accordingly, some embodiments include pharmaceutical compositions comprising: (a) a safe and therapeutically effective amount of a compound described herein, or pharmaceutically acceptable salts thereof and (b) a pharmaceutically acceptable carrier, diluent, excipient or combination thereof.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the TWEENS; wetting agents, such as sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort may be maximized as much as possible, although sometimes formulation considerations (e.g. drug stability) may necessitate less than optimal comfort. In the case that comfort cannot be maximized, the liquid may be formulated such that the liquid is tolerable to the patient for topical ophthalmic use. Additionally, an ophthalmically acceptable liquid may either be packaged for single use, or contain a preservative to prevent contamination over multiple uses.

For ophthalmic application, solutions or medicaments are often prepared using a physiological saline solution as a major vehicle. Ophthalmic solutions may preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

Ophthalmically acceptable antioxidants include, but are not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual unit dose of the active compounds described herein depends on the specific compound, and on the condition to be treated; the selection of the appropriate dose is well within the knowledge of the skilled artisan. In some embodiments, the dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. In some embodiments, the dose may be less than 100 mg/kg, 90 mg/kg, 80 mg/kg, 70 mg/kg, 60 mg/kg, 50 mg/kg, 40 mg/kg, 30 mg/kg, 25 mg/kg, 20 mg/kg, 10 mg/kg, 7.5 mg/kg, 5 mg/kg, 4 mg/kg, 2.5 mg/kg, or 1 mg/kg of body weight. Thus, for administration to a 70 kg person, the dosage range would be from about 17 mg to about 8000 mg, from about 35 mg or less to about 7000 mg or more, from about 70 mg to about 6000 mg, from about 100 mg to about 5000 mg, or from about 200 mg to about 3000 mg.

Method of Treatment

Some embodiments relate to a method for the treatment of a disease associated with thyroid hormone receptor β, comprising administering an effective amount of the compound described herein to a subject in need thereof.

In some embodiments, the disease is selected from the group consisting of obesity, hyperlipidemia, hypercholesterolemia and diabetes, and NASH (nonalcoholic steatohepatitis), atherosclerosis, cardiovascular diseases, hypothyroidism, and thyroid cancer.

Some embodiments relate to a method of agonizing thyroid hormone receptor β, comprising contacting the thyroid hormone receptor β with an effective amount of the compound described herein.

Some embodiments relate to a method for lowering cholesterol levels comprising administering an effective amount of the compound described herein to a subject in need thereof.

Some embodiments relate to a method for lowering triglyceride levels comprising administering an effective amount of the compound described herein to a subject in need thereof.

In some embodiments, the method described herein can include an additional therapeutic agent.

In some embodiments, the level of total T4 in the subject has a change of less than 50%, 20%, 10%, 5%, 1%, or 0.5% post administration compared to pre-administration levels. In some embodiments, the level of free T4 in the subject has a change of less than 50%, 20%, 10%, 5%, 1%, or 0.5% post administration compared to pre-administration levels. In some embodiments, the level of free T4 in the subject has a change in the range of about 0.5%-5%, 0.5%-10%, 0.5%-20%, 0.5%-30%, 0.5%-40%, 0.5%-50%, 0.5%-60%, 0.5%-70%, 0.5%-80%, 1%-5%, 1%-8%, 1%-10%, 1%-15%, 1%-20%, 1%-30%, 1%-40%, 1%-50%, 1%-60%, 2%-4%, 2%-5%, 2%-8%, 2%-10%, 2%-15%, 2%-20%, 2%-30%, 2%-40%, 2%-50%, 2%-60%, 3%-4%, 3%-5%, 3%-8%, 3%-10%, 3%-15%, 3%-20%, 3%-30%, 3%-40%, 3%-50%, 4%-5%, 4%-8%, 4%-10%, 4%-15%, 4%-20%, 4%-30%, 4%-40%, 4%-50%, 5%-8%, 5%-10%, 5%-15%, 5%-20%, 5%-30%, 5%-40%, 5%-50%, 5%-60%, 4%-8%, 10%-15%, 10%-20%, 10%-30%, 10%-40%, 10%-50%, 10%-60%, 15%-20%, 15%-30%, 15%-40%, 15%-50%, 15%-60%, 20%-30%, 20%-40%, 20%-50%, or 20%-60% post administration compared to pre-administration level.

In some embodiments, the level of total T3 in the subject has a change of less than 50%, 20%, 10%, 5%, 1%, or 0.5% post administration compared to pre-administration levels. In some embodiments, the level of free T3 in the subject has a change of less than 50%, 20%, 10%, 5%, 1%, or 0.5% post administration compared to pre-administration levels. In some embodiments, the level of free T3 in the subject has a change in the range of about 0.5%-5%, 0.5%-10%, 0.5%-20%, 0.5%-30%, 0.5%-40%, 0.5%-50%, 0.5%-60%, 0.5%-70%, 0.5%-80%, 1%-5%, 1%-8%, 1%-10%, 1%-15%, 1%-20%, 1%-30%, 1%-40%, 1%-50%, 1%-60%, 2%-4%, 2%-5%, 2%-8%, 2%-10%, 2%-15%, 2%-20%, 2%-30%, 2%-40%, 2%-50%, 2%-60%, 3%-4%, 3%-5%, 3%-8%, 3%-10%, 3%-15%, 3%-20%, 3%-30%, 3%-40%, 3%-50%, 4%-5%, 4%-8%, 4%-10%, 4%-15%, 4%-20%, 4%-30%, 4%-40%, 4%-50%, 5%-8%, 5%-10%, 5%-15%, 5%-20%, 5%-30%, 5%-40%, 5%-50%, 5%-60%, 4%-8%, 10%-15%, 10%-20%, 10%-30%, 10%-40%, 10%-50%, 10%-60%, 15%-20%, 15%-30%, 15%-40%, 15%-50%, 15%-60%, 20%-30%, 20%-40%, 20%-50%, or 20%-60% post administration compared to pre-administration level.

In some embodiments, the level of thyroid-stimulating hormone (THS) in the subject has a change of less than 50%, 20%, 10%, 5%, 1%, or 0.5% post administration compared to pre-administration levels. In some embodiments, the level of THS in the subject has a change in the range of about 0.5%-5%, 0.5%-10%, 0.5%-20%, 0.5%-30%, 0.5%-40%, 0.5%-50%, 0.5%-60%, 0.5%-70%, 0.5%-80%, 1%-5%, 1%-8%, 1%-10%, 1%-15%, 1%-20%, 1%-30%, 1%-40%, 1%-50%, 1%-60%, 2%-4%, 2%-5%, 2%-8%, 2%-10%, 2%-15%, 2%-20%, 2%-30%, 2%-40%, 2%-50%, 2%-60%, 3%-4%, 3%-5%, 3%-8%, 3%-10%, 3%-15%, 3%-20%, 3%-30%, 3%-40%, 3%-50%, 4%-5%, 4%-8%, 4%-10%, 4%-15%, 4%-20%, 4%-30%, 4%-40%, 4%-50%, 5%-8%, 5%-10%, 5%-15%, 5%-20%, 5%-30%, 5%-40%, 5%-50%, 5%-60%, 4%-8%, 10%-15%, 10%-20%, 10%-30%, 10%-40%, 10%-50%, 10%-60%, 15%-20%, 15%-30%, 15%-40%, 15%-50%, 15%-60%, 20%-30%, 20%-40%, 20%-50%, or 20%-60% post administration compared to pre-administration level.

Also provided are methods of reducing fat content in the liver or of preventing or treating steatosis, NASH or NAFLD in a subject in need thereof, the method comprising administering to the subject an effective amount of the compound described herein.

Some embodiments relate to a method for modulating cholesterol levels, for treating Obesity, hypercholesterolemia, hyperlipidemia, hypertriglyderidemia, and other metabolic diseases. In some embodiments, the metabolic disease is obesity, NASH, hypercholesterolemia, or hyperlipidemia. Some embodiments relate to a method for treating impaired glucose tolerance, insulin resistance, arteriosclerosis, atherosclerosis, coronary heart disease, heart failure, or diabetes. Some embodiments relate to the liver specific delivery of thyroid receptor ligands and the use of these compounds for the prevention and treatment of diseases responsive to modulation of T3-responsive genes in the liver. Some embodiments relate to treatment of hypothyroidism. The method described herein for treating the various listed diseases can be achieved using the compound described herein without affecting thyroid function, thyroid production of circulating iodinated thyronines such as T3 and T4, and/or the ratio of T3 to T4.

In one embodiment, the compound described herein can have a high therapeutic index for a use disclosed herein. Examples of said use disclosed herein includes but is not limited to reducing lipid levels, increasing the ratio of HDL to LDL or apoAI to LDL, reducing weight or preventing weight gain, maintaining or improving glycemic control, lowering blood glucose levels, increasing mitochondrial biogenesis, increasing expression of PGC-1, AMP activated protein kinase or nuclear respiratory factor, inhibiting hepatic gluconeogenesis or for the treatment or prevention of a disease or disorder selected from the group consisting of atherosclerosis, hypercholesterolemia, obesity, NASH, NAFLD, insulin resistance, diabetes, metabolic syndrome X, impaired glucose tolerance, hyperlipidemia, coronary heart disease, thyroid disease, thyroid cancer, depression, glaucoma, cardiac arrhythmias, heart failure, and osteoporosis. Examples wherein the property or function is a cardiac property/function include but is not limited to cardiac hypertrophy (heart weight to body weight ratio), heart rate, and various hemodynamic parameters, including systolic and diastolic arterial pressure, end systolic left ventricular pressure and maximal speeds of contraction and relaxation.

Compound I can have a higher therapeutic index (TI) than the compound MB07811 when used in the treatment methods described herein. In some embodiments, compound I can have a TI that is at least abut 2, 3, 4, 5, 6, 7, 8, 9, 10, 20, 30, 40, 50, 60, 70, 80, 90, 100, 150, 200 times greater than compound MB07811. In some embodiments, compound I can have a TI that is in the range of about 2-200, 2-100, 2-50, 2-25, 2-10, 5-200, 5-100, 5-50, 5-10, 10-200, 10-100, 10-50, 10-25, 20-100, 20-50, or 50-100 times greater than compound MB07811.

In some embodiments, the compound described herein has a plasma half-life of less than about 1, 2, 3, 4, 5, 6, 7, 8, 9, 10, 12, 14, 16, 18, 20, or 25 hours. In some embodiments, the compound described herein has a plasma half-life of greater than about 1, 2, 3, 4, 5, 6, 7, 8, 9, 10, 12, 14, 16, 18, 20, or 25 hours. In some embodiments, the compound described herein has a plasma half-life in the range of about 1-25, 1-20, 1-18, 1-15, 1-10, 1-8, 1-6, 1-4, 1-2, 2-20, 2-15, 2-10, 2-8, 2-6, 2-4, 3-20, 3-15, 3-10, 3-9, 3-6, 3-5, 4-20, 4-18, 4-15, 4-10, 4-8, 4-6, 5-20, 5-15, 5-10, 5-8, 5-6, 6-20, 6-15, 6-10, 6-8, 8-20, 8-15, 8-10, 10-20, 10-15, 12-20, 12-15, or 15-20 hours.

In some embodiments, the LDL level of the subject is reduced by at least 10% or 20% post administration compared to pre-administration level. In some embodiments, the LDL level of the subject is reduced by at least about 2%, 5%, 10%, 15%, 18%, 20%, 25%, 28%, 30%, 35%, 40%, 45%, 50%, 55%, 60%, 70%, 80%, 90%, or 95% post administration compared to pre-administration level. In some embodiments, the LDL level of the subject is reduced in the range of about 2%-90%, 5%-10%, 5%-20%, 5%-30%, 5%-40%, 5%-50%, 5%-60%, 5%-70%, 5%-80%, 5%-90%, 10%-20%, 10%-30%, 10%-40%, 10%-50%, 10%-60%, 10%-70%, 10%-80%, 10%-90%, 20%-30%, 20%-40%, 20%-50%, 20%-60%, 20%-70%, 20%-80%, 20%-90%, 30%-40%, 30%-50%, 30%-60%, 30%-70%, 30%-80%, 30%-90%, 40%-50%, 40%-60%, 40%-70%, 40%-80%, 40%-90%, 50%-60%, 50%-70%, 50%-80%, 50%-90%, 60%-70%, 60%-80%, 60%-90% post administration compared to pre-administration level.

In some embodiments, the triglyceride level of the subject is reduced by at least 10% or 20% post administration compared to pre-administration level. In some embodiments, the triglyceride level of the subject is reduced by at least about 2%, 5%, 10%, 15%, 18%, 20%, 25%, 28%, 30%, 35%, 40%, 45%, 50%, 55%, 60%, 70%, 80%, 90%, or 95% post administration compared to pre-administration level. In some embodiments, the triglyceride level of the subject is reduced in the range of about 2%-90%, 5%-10%, 5%-20%, 5%-30%, 5%-40%, 5%-50%, 5%-60%, 5%-70%, 5%-80%, 5%-90%, 10%-20%, 10%-30%, 10%-40%, 10%-50%, 10%-60%, 10%-70%, 10%-80%, 10%-90%, 20%-30%, 20%-40%, 20%-50%, 20%-60%, 20%-70%, 20%-80%, 20%-90%, 30%-40%, 30%-50%, 30%-60%, 30%-70%, 30%-80%, 30%-90%, 40%-50%, 40%-60%, 40%-70%, 40%-80%, 40%-90%, 50%-60%, 50%-70%, 50%-80%, 50%-90%, 60%-70%, 60%-80%, 60%-90% post administration compared to pre-administration level.

In some embodiments, the ratio of the HDL and LDL can be increased by at least about at least about 2%, 5%, 10%, 15%, 18%, 20%, 25%, 28%, 30%, 35%, 40%, 45%, 50%, 55%, 60%, 70%, 80%, 90%, or 95% post administration compared to pre-administration level. In some embodiments, the ratio of the HDL and LDL can be increased by a range of about 2%-90%, 5%-10%, 5%-20%, 5%-30%, 5%-40%, 5%-50%, 5%-60%, 5%-70%, 5%-80%, 5%-90%, 10%-20%, 10%-30%, 10%-40%, 10%-50%, 10%-60%, 10%-70%, 10%-80%, 10%-90%, 20%-30%, 20%-40%, 20%-50%, 20%-60%, 20%-70%, 20%-80%, 20%-90%, 30%-40%, 30%-50%, 30%-60%, 30%-70%, 30%-80%, 30%-90%, 40%-50%, 40%-60%, 40%-70%, 40%-80%, 40%-90%, 50%-60%, 50%-70%, 50%-80%, 50%-90%, 60%-70%, 60%-80%, 60%-90% post administration compared to pre-administration level.

In some embodiments, the compound can be administered parenterally. In some embodiments, the compound can be administered orally. In some embodiments, the compound can be administered intravenously or intramuscularly.

In some embodiments, the subject is a human. In some embodiments, the subject is a mammal.

Further embodiments include administering a combination of compounds to a subject in need thereof. A combination can include a compound, composition, pharmaceutical composition described herein with an additional medicament.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

Moreover, the compound described herein can be administered in combination with other pharmaceutical agents that are used to lower serum cholesterol such as a cholesterol biosynthesis inhibitor or a cholesterol absorption inhibitor, especially a HMG-CoA reductase inhibitor, or a HMG-CoA synthase inhibitor, or a HMG-CoA reductase or synthase gene expression inhibitor, a cholesteryl ester transfer protein (CETP) inhibitor (e.g., torcetrapib), a bile acid sequesterant (e.g., cholestyramine (Questran®), colesevelam and colestipol (Colestid®)), or a bile acid reabsorption inhibitor (see, for example, U.S. Pat. No. 6,245,744, U.S. Pat. No. 6,221, 897, U.S. Pat. No. 6,277,831, EP 0683 773, EP 0683 774, all of which are incorporated herein by reference), a cholesterol absorption inhibitor as described (e.g., ezetimibe, tiqueside, pamaqueside or see, e.g., in WO 0250027, which is incorporated herein by reference), a PPARalpha agonist, a mixed PPAR alpha/gamma agonist such as, for example, AZ 242 (Tesaglitazar, (S)-3-(4-[2-(4-methanesulfony-loxyphenyl) ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876, all of which are incorporated herein by reference; a MTP inhibitor such as, for example, implitapide, a fibrate, an ACAT inhibitors (e.g., avasimibe), an angiotensin II receptor antagonist, a squalene synthetase inhibitor, a squalene epoxidase inhibitor, a squalene cyclase inhibitor, combined squalene epoxidase/squalene cyclase inhibitor, a lipoprotein lipase inhibitor, an ATP citrate lyase inhibitor, lipoprotein(a) antagonist, an antioxidant or niacin (e.g., slow release niacin). The compound described herein may also be administered in combination with a naturally occurring compound that act to lower plasma cholesterol levels. Such naturally occurring compounds are commonly called nutraceuticals and include, for example, garlic extract and niacin.

In one aspect, the HMG-CoA reductase inhibitor is from a class of therapeutics commonly called statins. Examples of HMG-CoA reductase inhibitors that may be used include but are not limited to lovastatin (MEVACOR; see U.S. Pat. Nos. 4,231,938; 4,294,926; 4,319,039), simvastatin (ZOCOR; see U.S. Pat. Nos. 4,444,784; 4,450,171, 4,820,850; 4,916,239, all of which are incorporated herein by reference), pravastatin (PRAVACHOL; see U.S. Pat. Nos. 4,346,227; 4,537, 859; 4,410,629; 5,030,447 and 5,180,589, all of which are incorporated herein by reference), lactones of pravastatin (see U.S. Pat. No. 4,448,979, which is incorporated herein by reference), fluvastatin (LESCOL; see U.S. Pat. Nos. 5,354,772; 4,911,165; 4,739,073; 4,929,437; 5,189,164; 5,118,853; 5,290,946; 5,356,896, all of which are incorporated herein by reference), lactones of fluvastatin, atorvastatin (LIPITOR; see U.S. Pat. Nos. 5,273,995; 4,681,893; 5,489,691; 5,342,952, all of which are incorporated herein by reference), lactones of atorvastatin, cerivastatin (also known as rivastatin and BAYCHOL; see U.S. Pat. No. 5,177,080, and European Application No. EP-491226A), lactones of cerivastatin, rosuvastatin (Crestor; see U.S. Pat. Nos. 5,260,440 and RE37314, and European Patent No. EP521471, all of which are incorporated herein by reference), lactones of rosuvastatin, itavastatin, nisvastatin, visastatin, atavastatin, bervastatin, compactin, dihydrocompactin, dalvastatin, fluindostatin, pitivastatin, mevastatin (see U.S. Pat. No. 3,983,140, which is incorporated herein by reference), and velostatin (also referred to as synvinolin). Other examples of HMG-CoA reductase inhibitors are described in U.S. Pat. Nos. 5,217,992; 5,196,440; 5,189, 180; 5,166,364; 5,157,134; 5,110,940; 5,106,992; 5,099, 035; 5,081,136; 5,049,696; 5,049,577; 5,025,017; 5,011, 947; 5,010,105; 4,970,221; 4,940,800; 4,866,058; 4,686, 237; 4,647,576; European Application Nos. 0142146A2 and 0221025A1; and PCT Application Nos. WO 86/03488 and WO 86/07054, all of which are incorporated herein by reference. Also included are pharmaceutically acceptable forms of the above. All of the above references are incorporated herein by reference.

Non-limiting examples of suitable bile acid sequestrants include cholestyramine (a styrene-divinylbenzene copolymer containing quaternary ammonium cationic groups capable of binding bile acids, such as QUESTRAN or QUESTRAN LIGHT cholestyramine which are available from Bristol-Myers Squibb), colestipol (a copolymer of diethylenetriamine and 1-chloro-2,3-epoxypropane, such as COLESTID tablets which are available from Pharmacia), colesevelam hydrochloride (such as WelChol Tablets (poly (allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl)alkylamines and poliglusam, insoluble quaternized polystyrenes, saponins and mixtures thereof. Other useful bile acid sequestrants are disclosed in PCT Patent Applications Nos. WO 97/11345 and WO 98/57652, and U.S. Pat. Nos. 3,692,895 and 5,703,188 which are incorporated herein by reference. Suitable inorganic cholesterol sequestrants include bismuth salicylate plus montmorillonite clay, aluminum hydroxide and calcium carbonate antacids.

In the above description, a fibrate base compound is a medicament for inhibiting synthesis and secretion of triglycerides in the liver and activating lipoprotein lipase, thereby lowering the triglyceride level in the blood. Examples include bezafibrate, beclobrate, binifibrate, ciprofibrate, clinofibrate, clofibrate, clofibric acid, ethofibrate, fenofibrate, gemfibrozil, nicofibrate, pirifibrate, ronifibrate, simfibrate and theofibrate. Such an ACAT inhibitor includes, for example: a compound having the general formula (I) disclosed in WO 92/09561 [preferably FR-129169, of which the chemical name is N-(1,2-diphenylethyl)-2-(2-octyloxyphenyl)acetamide]; a compound having the general formula (I) including a pharmacologically acceptable salt/co-crystal, ester or prodrug thereof disclosed in the Japanese Patent Publication (Kohyo) Hei 8-510256 (WO 94/26702, U.S. Pat. No. 5,491,172) {preferably CI-1011, of which the chemical name is 2,6-diisopropylphenyl-N-[(2,4,6-tr-iisopropylphenyl)acetyl]sulfamate, and CI-1011 described herein including a pharmacologically acceptable salt/co-crystal, ester or prodrug thereof; a compound having the general formula (I) including a pharmacologically acceptable salt/co-crystal, ester or prodrug thereof disclosed in EP 421-441 (U.S. Pat. No. 5,120,738) {preferably F-1394, of which the chemical name is (1S,2S)-2-[3-(2,2-dimet-hylpropyl)-3-nonylureido] cyclohexan-1-yl 3-[(4R)—N-(2,2,5,5-tetramethyl-1, -3-dioxane-4-carbonyl)amino]propionate, and F-1394 including a pharmacologically acceptable salt/co-crystal, ester or prodrug thereof}; a compound including a pharmacologically acceptable salt/co-crystal, ester or prodrug thereof disclosed in the Japanese Patent Publication (Kohyo) 2000-500771 (WO 97/19918, U.S. Pat. No. 5,990,173, all of which are incorporated herein by reference) {preferably F-12511, of which the chemical name is (S)-2',3',5'-trimethyl-4'-hydroxy-.alpha.-dodecylthio-.alpha.-phenylaceta-nilide, and F-12511 including a pharmacologically acceptable salt/co-crystal, ester or prodrug thereof.]; a compound having the general formula (I) including a pharmacologically acceptable salt/co-crystal, ester or prodrug thereof disclosed in the Japanese Patent Publication (Kokai) Hei 10-195037 (EP 790240, U.S. Pat. No. 5,849,732, all of which are incorporated herein by reference) [preferably T-2591, of which the chemical name is 1-(3-t-butyl-2-hydroxy-5-methoxyphenyl)-3-(2-cyclohexylethyl)-3-(4-diethylaminophenyl)urea, and T-2591 including a pharmacologically acceptable salt/co-crystal, ester or prodrug thereof.]; a compound having the general formula (I) including a pharmacologically acceptable salt/co-crystal, ester or prodrug thereof disclosed in WO 96/26948 [preferably FCE-28654, of which the chemical name is 1-(2,6-diisopropylphenyl)-3-[(4R,5R)-4,5-dimethyl-2-(4-phosphonophenyl)-1,3-dioxolan-2-ylmethyl] urea, including a pharmacologically acceptable salt/co-crystal, ester or prodrug thereof.}; a compound having the general formula (I) or a pharmacologically acceptable salt thereof disclosed in the specification of WO 98/54153 (EP 987254), which is incorporated herein by reference {preferably K-10085, of which the chemical name is N-[2,4-bis(methylthio)-6-methyl-3-pyridyl]-2-[4-[2-(oxazolo[4,5-b]pyridine-2-ylthio)ethyl]piperazin-1-yl]acetamide, including a pharmacologically acceptable salt/co-crystal, ester or prodrug thereof.}; a compound having the general formula (I) disclosed in WO 92/09572 (EP 559898, U.S. Pat. No. 5,475,130, all of which are incorporated herein by reference) [preferably HL-004, of which the chemical name is N-(2,6-diisopropylphenyl)-2-tetradecylthioacetamide.]; a compound having the general formula (I) including a pharmacologically acceptable salt/co-crystal, ester or prodrug thereof disclosed in the Japanese Patent Publication (Kokai) Hei 7-82232 (EP 718281, which is incorporated herein by reference) {preferably NTE-122, of which the chemical name is trans-1,4-bis[1-cyclohexyl-3-(4-dimethylaminophenyl)urei-domethyl]cyclohexane, and NTE-122 includes pharmacologically acceptable salts of NTE-122.}; a compound including a pharmacologically acceptable salt/co-crystal, ester or prodrug thereof disclosed in the Japanese Patent Publication (Kohyo) Hei 10-510512 (WO 96/10559, which is incorporated herein by reference) {preferably FR-186054, of which the chemical name is 1-benzyl-1-(pyrazol-3-yl)benzyl]-3-[2,4-bis(methylthio)-6-methyl-pyridi-n-3-yl]urea, and FR-186054 including a pharmacologically acceptable salt/co-crystal, ester or prodrug thereof}; a compound having the general formula (I) including a pharmacologically acceptable salt/co-crystal, ester or prodrug thereof disclosed in WO 96/09287 (EP 0782986, U.S. Pat. No. 5,990,150, all of which are incorporated herein by reference) [preferably N-(1-pentyl-4,6-dimethylindolin-7-yl)-2,2-dime-thylpropaneamide, and including a pharmacologically acceptable salt/co-crystal, ester or prodrug thereof]; and a compound having the general formula (I) including a pharmacologically acceptable salt/co-crystal, ester or prodrug thereof disclosed in WO 97/12860 EP 0866059, U.S. Pat. No. 6,063,806, all of which are incorporated herein by reference) [preferably N-(1-octyl-5-carboxymethyl-4,6-dimethylindolin-7-yl)-2,2-dimethylpropaneamide, including a pharmacologically acceptable salt/co-crystal, ester or prodrug thereof]. The ACAT inhibitor preferably is a compound selected from the group consisting of FR-129169, CI-1011, F-1394, F-12511, T-2591, FCE-28654, K-10085, HL-004, NTE-122, FR-186054, N-(1-octyl-5-carboxymethyl-4,6-dimethylindolin-7-yl)-2,2-dimethylpropaneamide (hereinafter referred as compound A), and N-(1-pentyl-4,6-dimethylindolin-7-yl)-2,2-dimethyl-propan-eamide (hereinafter referred as compound B), including a pharmacologically acceptable salt/co-crystal, ester or prodrug thereof. The ACAT inhibitor more preferably is a compound selected from the group consisting of CI-1011, F-12511, N-(1-octyl-5-carboxymethyl-4,6-dimethylindolin-7-yl)-2,2-dimethylpropaneamide (compound A), and N-(1-pentyl-4,6-dimethylindolin-7-yl)-2,2-dimethylpropaneamide (compound B), including a pharmacologically acceptable salt/co-crystal, ester or prodrug thereof; most preferred is N-(1-octyl-5-carboxymethyl-4,6-dimethylindolin-7-yl)-2,2-ditnethylpropanea-mide (compound A).

An angiotensin II receptor antagonist includes, for example, a biphenyl tetrazole compound or biphenylcarboxylic acid derivative such as: a compound having the general formula (I) including a pharmacologically acceptable salt/co-crystal, ester or prodrug thereof disclosed in the Japanese Patent Publication (Kokai) Sho 63-23868 (U.S. Pat. No. 5,138,069) {preferably losartan, of which the chemical name is 2-butyl-4-chloro-1-[2'-(1H-tetrazol-5-yl)biphe-nyl-4-ylmethyl]-1H-imidazol-5-methanol, and losartan including a pharmacologically acceptable salt/co-crystal, ester or prodrug thereof}; a compound having the general formula (I) including a pharmacologically acceptable salt/co-crystal, ester or prodrug thereof disclosed in the Japanese Patent Publication (Kohyo) Hei 4-506222 (WO 91/14679, which is incorporated herein by reference) {preferably irbesartan, of which the chemical name is 2-N-butyl-4-spirocyclopentane-1-[2'-(1H-tetrazol-5-yl)bi-phenyl-4-ylmethyl]-2-imidazoline-5-one, and irbesartan including a pharmacologically acceptable salt/co-crystal, ester or prodrug thereof.}; a compound having the general formula (I), an ester thereof, including a pharmacologically acceptable salt/co-crystal, ester or prodrug thereof disclosed in the Japanese Patent Publication (Kokai) Hei 4-235149 (EP 433983, which is incorporated herein by reference) {preferably valsartan, of which the chemical name is (S)—N-valeryl-N-[2'-(1H-tetrazol-5-yl)biphenyl-4-ylmethyl]valine, and valsartan including a pharmacologically acceptable salt/co-crystal, ester or prodrug thereof.}; a carboxylic acid derivative having the general formula (I), including a pharmacologically acceptable salt/co-crystal, ester or prodrug thereof disclosed in the Japanese Patent Publication (Kokai) Hei 4-364171 (U.S. Pat. No. 5,196,444) {preferably candesartan, of which the chemical name is 1-(cyclohexyloxycarbonyloxy)ethyl 2-ethoxy-1-[2'-(1H-etrazol-5-yl)biphen-yl-4-ylmethyl]-1H-benzimidazole-7-carboxylate, and candesartan including a pharmacologically acceptable salt/co-crystal, ester or prodrug thereof (TCV-116 or the like), including a pharmacologically acceptable salt/co-crystal, ester or prodrug thereof.}; a carboxylic acid derivative having the general formula (I), including a pharmacologically acceptable salt/co-crystal, ester or prodrug thereof disclosed in the Japanese Patent Publication (Kokai) Hei 5-78328 (U.S. Pat. No. 5,616,599, which is incorporated herein by reference) {preferably olmesartan, of which the chemical name is (5-methyl-2-oxo-1,3-dioxolen-4-yl)methyl 4-(1-hydroxy-1-methylethyl)-2-pr-opyl-1-[2'-(1H-tetrazol-5-yl)biphenyl-4-ylmethyl]imidazole-5-carboxylate, and olmesartan includes carboxylic acid derivatives thereof, pharmacologically acceptable esters of the carboxylic acid derivatives (CS-866 or the like), including a pharmacologically acceptable salt/co-crystal, ester or prodrug thereof}; and a compound having the general formula (I), including a pharmacologically acceptable salt/co-crystal, ester or prodrug thereof disclosed in the Japanese Patent Publication (Kokai) Hei 4-346978 (U.S. Pat. No. 5,591,762, EP 502,314, which are incorporated herein by reference) {preferably telmisartan, of which the chemical name is 4'-[[2-n-propyl-4-methyl-6-(1-methylbenzimidazol-2-yl)-benzimidazol-1-yl]-methyl]biphenyl-2-carboxylate, including a pharmacologically acceptable salt/co-crystal, ester or prodrug thereof}. The angiotensin II receptor antagonist preferably is losartan, irbesartan, valsartan, candesartan, olmesartan, or telmisartan; more preferred is losartan or olmesartan; and most preferred is olmesartan.

In addition to being useful in treating or preventing certain diseases and disorders, combination therapy with the compound described herein may be useful in reducing the dosage of the second drug or agent (e.g., atorvastatin).

In addition, the compound described herein can be used in combination with an apolipoprotein B secretion inhibitor and/or microsomal triglyceride transfer protein (MTP) inhibitor. Some apolipoprotein B secretion inhibitors and/or MTP inhibitors are disclosed in U.S. Pat. No. 5,919,795, which is incorporated herein by reference.

Any HMG-CoA reductase inhibitor may be employed as an additional compound in the combination therapy aspect described herein. The term HMG-CoA reductase inhibitor refers to a compound that inhibits the biotransformation of hydroxymethylglutaryl-coenzyme A to mevalonic acid as catalyzed by the enzyme HMG-CoA reductase. Such inhibition may be determined readily by one of skill in the art according to standard assays (e.g., *Methods of Enzymology*, 71: 455-509 (1981); and the references cited therein, which is incorporated herein by reference). A variety of these compounds are described and referenced below. U.S. Pat. No. 4,231,938, which is incorporated herein by reference discloses certain compounds isolated after cultivation of a microorganism belonging to the genus *Aspergillus*, such as lovastatin. Also U.S. Pat. No. 4,444,784 discloses synthetic derivatives of the aforementioned compounds, such as simvastatin. Additionally, U.S. Pat. No. 4,739,073, which is incorporated herein by reference, discloses certain substituted indoles, such as fluvastatin. Further, U.S. Pat. No. 4,346,227, which is incorporated herein by reference, discloses ML-236B derivatives, such as pravastatin. In addition, EP 491,226 teaches certain pyridyldihydroxyheptenoic acids, such as rivastatin. Also, U.S. Pat. No. 4,647,576, which is incorporated herein by reference, discloses certain 6-[2-(substituted-pyrrol-1-yl)-alkyl]-pyran-2-ones such as atorvastatin. Other HMG-CoA reductase inhibitors will be known to those skilled in the art. Examples of currently or previously marketed products containing HMG-CoA reductase inhibitors include cerivastatin Na, rosuvastatin Ca, fluvastatin, atorvastatin, lovastatin, pravastatin Na and simvastatin.

Any HMG-CoA synthase inhibitor may be used as an additional compound in the combination therapy. The term HMG-CoA synthase inhibitor refers to a compound that inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., *Methods of Enzymology* 35: 155-160 (1975); and *Methods of Enzymology*, 110: 19-26 (1985); and the references cited therein). A variety of these compounds are described and referenced below. U.S. Pat. No. 5,120,729 discloses certain beta-lactam derivatives. U.S. Pat. No. 5,064,856 discloses certain spiro-lactone derivatives prepared by culturing the microorganism MF5253. U.S. Pat. No. 4,847,271 discloses certain oxetane compounds such as 11-(3-hydroxymethyl-4-oxo-2-oxetayl)-3,5,7-trimethyl-2,4-undecadienoic acid derivatives, all of which are incorporated herein by reference. Other HMG-CoA synthase inhibitors known to those skilled in the art can also be used in the methods, compositions and kits described herein.

Any compound that decreases HMG-CoA reductase gene expression may be used as an additional compound in the combination therapy described herein. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (*Methods of Enzymology*, 110: 9-19 (1985)). Several such compounds are described and referenced below; however, other inhibitors of HMG-CoA reductase gene expression will be known to those skilled in the art, for example, U.S. Pat. No. 5,041,432, which is incorporated herein by reference, discloses certain 15-substituted lanosterol derivatives that are inhibitors of HMG-CoA reductase gene expression. Other oxygenated sterols that suppress the biosynthesis of HMG-CoA reductase are discussed by E. I. Mercer (*Prog. Lip. Res.*, 32:357-416 (1993)), which is incorporated herein by reference.

Any compound having activity as a CETP inhibitor can serve as the second compound in the combination therapy aspect. The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below; however, other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815-816 (1996), and *Bioorg. Med. Chem. Lett.*, 6:1951-1954 (1996), respectively, which are incorporated herein by reference.

Any ACAT inhibitor can serve as an additional compound in the combination therapy. The term ACAT inhibitor refers to a compound that inhibits the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research*, 24:1127 (1983). A variety of these compounds are described and referenced below; however, other ACAT inhibitors will be known to those skilled in the art. U.S. Pat. No. 5,510,379 discloses certain carboxysulfonates, while WO 96/26948 and WO 96/10559 both disclose urea derivatives having ACAT inhibitory activity, which are incorporated herein by reference.

Any compound having activity as a squalene synthetase inhibitor can serve as an additional compound in the combination therapy. The term squalene synthetase inhibitor refers to compounds that inhibit the condensation of two molecules of farnesylpyrophosphate to form squalene, a reaction that is catalyzed by the enzyme squalene synthetase. Such inhibition is readily determined by those skilled in the art according to standard methodology (*Methods of Enzymology* 15:393-454 (1969); and *Methods of Enzymology* 110: 359-373 (1985); and references cited therein, which are incorporated herein by reference). A summary of squalene synthetase inhibitors has been complied in *Curr. Op. Ther Patents*, 861-4, (1993). EP 0 567 026 A1 discloses certain 4,1-benzoxazepine derivatives as squalene synthetase inhibitors and their use in the treatment of hypercholesterolemia and as fungicides. EP 0 645 378 A1 discloses certain seven- or eight-membered heterocycles as squalene synthetase inhibitors and their use in the treatment and prevention hypercholesterolemia and fungal infections. EP 0 645 377 A1 discloses certain benzoxazepine derivatives as squalene synthetase inhibitors useful for the treatment of hypercholesterolemia or coronary sclerosis. EP 0 611 749 A1 discloses certain substituted amic acid derivatives useful for the treatment of arteriosclerosis. EP 0 705 607 A2 discloses certain condensed seven- or eight-membered heterocyclic compounds useful as antihypertriglyceridemic agents. WO 96/09827 discloses certain combinations of cholesterol absorption inhibitors and cholesterol biosynthesis inhibitors including benzoxazepine derivatives and benzothiazepine derivatives. EP 0 701 725 A1 discloses a process for preparing certain optically-active compounds, including benzoxazepine derivatives, having plasma cholesterol and triglyceride lowering activities. All of the cited references are incorporated herein by reference.

Other compounds that are currently or previously marketed for hyperlipidemia, including hypercholesterolemia, and which are intended to help prevent or treat atherosclerosis, include bile acid sequestrants, such as colestipol HCl and cholestyramine; and fibric acid derivatives, such as clofibrate, fenofibrate, and gemfibrozil. These compounds can also be used in combination with the compound described herein.

It is also contemplated that the compound described herein can be administered with a lipase inhibitor and/or a glucosidase inhibitor, which are typically used in the treatment of conditions resulting from the presence of excess triglycerides, free fatty acids, cholesterol, cholesterol esters or glucose including, inter alia, obesity, hyperlipidemia, hyperlipoproteinemia, Syndrome X, and the like.

In a combination with the compound described herein, any lipase inhibitor or glucosidase inhibitor may be employed. In one aspect lipase inhibitors comprise gastric or pancreatic lipase inhibitors. In a further aspect glucosidase inhibitors comprise amylase inhibitors. Examples of glucosidase inhibitors are those inhibitors selected from the group consisting of acarbose, adiposine, voglibose, miglitol, emiglitate, camiglibose, tendamistate, trestatin, pradimicin-Q and salbostatin. Examples of amylase inhibitors include tendamistat and the various cyclic peptides related thereto disclosed in U.S. Pat. No. 4,451,455, AI-3688 and the various cyclic polypeptides related thereto disclosed in U.S. Pat. No. 4,623,714, and trestatin, consisting of a mixture of trestatin A, trestatin B and trestatin C and the various trehalose-containing aminosugars related thereto disclosed in U.S. Pat. No. 4,273,765, all of which are incorporated herein by reference.

A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid phospholipid micelles, which are subsequently absorbed at the level of the brush border of the small intestine. The micelles eventually enter the peripheral circulation as chylomicrons. Accordingly, compounds, including lipase inhibitors that selectively limit or inhibit the absorption of ingested fat precursors are useful in the treatment of conditions including obesity, hyperlipidemia, hyperlipoproteinemia, Syndrome X, and the like.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K Abrams, et al., *Gastroenterology* 92: 125 (1987), which is incorporated herein by reference.

A variety of lipase inhibitors are known to one of ordinary skill in the art. In some embodiments, lipase inhibitors are those inhibitors that are selected from the group consisting of lipstatin, tetrahydrolipstatin (orlistat), FL-386, WAY-121898, Bay-N-3176, valilactone, esterastin, ebelactone A, ebelactone B and RHC 80267.

The pancreatic lipase inhibitors lipstatin, 2S, 3S, SS, 7Z, 1OZ)-5-[(S)-2-formamido-4-methyl-valeryloxy]-2-hexyl-3-hydroxy-7,1 (t-hexadecan oic acid lactone, and tetrahydro-lipstatin (orlistat), 2S, 3S, 5S)-5-[(S)-2-formamido-4-methyl-valeryloxy]-2-hexyl-3-hydroxy-hexadecanoic acid lactone, and the variously substituted N-formylleucine derivatives and stereoisomers thereof, are disclosed in U.S. Pat. No. 4,598,089, which is incorporated herein by reference.

The pancreatic lipase inhibitor FL-386, 1-[4-(2-methyl-propyl)cyclohexyl]-2-[(phenylsulfonyl)oxy]-ethanone, and the variously substituted sulfonate derivatives related thereto, are disclosed in U.S. Pat. No. 4,452,813, which is incorporated herein by reference.

The pancreatic lipase inhibitor WAY-121898, 4-phenoxy-phenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151, all of which are incorporated herein by reference.

The lipase inhibitor Bay-N-3176, N-3-trifluoromethyl-phenyl-N'-3-chloro-4-trifluoromethylphenylurea, and the various urea derivatives 65 related thereto, are disclosed in U.S. Pat. No. 4,405,644, which is incorporated herein by reference.

The pancreatic lipase inhibitor valilactone, and a process for the preparation thereof by the microbial cultivation of Actinomycetes strain MG147CF$_2$, are disclosed in Kitahara, et al., *J. Antibiotics*, 40(11): 1647-50 (1987), which is incorporated herein by reference.

The lipase inhibitor esteracin, and certain processes for the preparation thereof by the microbial cultivation of *Streptomyces* strain ATCC 31336, are disclosed in U.S. Pat. Nos. 4,189,438 and 4,242,453, all of which are incorporated herein by reference.

The pancreatic lipase inhibitors ebelactone A and ebelactone B, and a process for the preparation thereof by the microbial cultivation of Actinomycetes strain MG7-G1, are disclosed in Umezawa, et al., *J. Antibiotics,* 33, 1594-1596 (1980). The use of ebelactones A and B in the suppression of monoglyceride formation is disclosed in Japanese Kokai 08-143457, published Jun. 4, 1996, which is incorporated herein by reference.

The lipase inhibitor RHC 80267, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen,* 562: 205-29 (1949), which is incorporated herein by reference.

The ability of RHC 80267 to inhibit the activity of myocardial lipoprotein lipase is disclosed in Carroll et al., *Lipids,* 27 305-7 (1992) and Chuang et al., *J. Mol. Cell. Cardiol.,* 22: 1009-16 (1990), all of which are incorporated herein by reference.

In another embodiment, the compound described herein can be used in combination with an additional anti-obesity agent. The additional anti-obesity agent in one aspect is selected from the group consisting of a 3-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, a leptin analog, a leptin receptor agonist, a galanin antagonist, a lipase inhibitor, a bombesin agonist, a neuropeptide-Y antagonist, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, and a ciliary neurotrophic factor.

In an additional aspect the anti-obesity agents comprise those compounds selected from the group consisting of sibutramine, fenfluramine, dexfenfluramine, bromocriptine, phentermine, ephedrine, leptin, phenylpropanolamine pseudoephedrine, {4-[2-(2-[6-aminopyridin-3-yl]-2(R)-hydroxyethylamino)ethoxy]phenyl} acetic acid, {4-[2-(2-[6-aminopyridin-3-yl]-2(R)-hydroxyethylamino)ethoxy]phenyl}benzoic acid, {4-[2-(2-[6-aminopyridin-3-yl]-2(R)-hydroxyethylamino)ethoxy]phenyl}propionic acid, and {4-[2-(2-[6-aminopyridin-3-yl]-2(R)-hydroxyethylamino)ethoxy]phenoxy}acetic acid.

In some embodiments, the prevention or treatment of diabetes can include impaired glucose tolerance, insulin resistance, insulin dependent diabetes mellitus (Type I) and non-insulin dependent diabetes mellitus (NIDDM or Type II). Also included in the prevention or treatment of diabetes are the diabetic complications, such as neuropathy, nephropathy, retinopathy or cataracts.

In one aspect the type of diabetes to be treated by the compound described herein is non-insulin dependent diabetes mellitus, also known as Type II diabetes or NIDDM.

Diabetes can be treated by administering to a patient having diabetes (Type I or Type II), insulin resistance, impaired glucose tolerance, or any of the diabetic complications such as neuropathy, nephropathy, retinopathy or cataracts, a therapeutically effective amount of the compound described herein. It is also contemplated that diabetes be treated by administering the compound described herein along with other agents that can be used to prevent or treat diabetes.

Representative agents that can be used to treat diabetes in combination with the compound described herein include insulin and insulin analogs (e.g., LysPro insulin); GLP-1 (7-37) (insulinotropin) and GLP-1 (7-36)-NH$_2$. Agents that enhance insulin secretion, e.g., eblorpropamide, glibenclamide, tolbutamide, tolazamide, acetohexamide, glypizide, glimepiride, repaglinide, nateglinide, meglitinide; biguanides: metformin, phenformin, buformin; A2-antagonists and imidazolines: midaglizole, isaglidole, deriglidole, idazoxan, efaroxan, fluparoxan; other insulin secretagogues linogliride, A-4166; glitazones: ciglitazone, pioglitazone, englitazone, troglitazone, darglitazone, BR149653; fatty acid oxidation inhibitors: clomoxir, etomoxir; a-glucosidase inhibitors: acarbose, miglitol, emiglitate, voglibose, MDL25,637, camiglibose, MDL-73,945; ˜3-agonists: BRL 35135, BRL 37344, RO 16-8714, ICI D7114, CL 316,243; phosphodiesterase inhibitors: −386,398; lipid-lowering agents benfluorex; antiobesity agents: fenfiuramine; vanadate and vanadium complexes (e.g., bis(cysteinamide N-octyl) oxovanadium) and peroxovanadium complexes; amylin antagonists; glucagon antagonists; gluconeogenesis inhibitors; somatostatin analogs; antilipolytic agents: nicotinic acid, acipimox, WAG 994. Also contemplated to be used in combination with the compound described herein are pramlintide (Symlin™), AC 2993 and nateglinide. Any agent or combination of agents can be administered as described above.

In addition, the compound described herein can be used in combination with one or more aldose reductase inhibitors, DPPIV inhibitor, glycogen phosphorylase inhibitors, sorbitol dehydrogenase inhibitors, NHE-1 inhibitors and/or glucocorticoid receptor antagonists.

Any compound having activity as a fructose-1,6-bisphosphatase (FBPase) inhibitor can serve as the second compound in the combination therapy (e.g., 2-Amino-5-isobutyl-4-{2-[5-(N,N'-bis((S)-1-ethoxycarbonyl)ethyl) phosphonamido]furanyl}thiazoles). FBPase is a key regulatory enzyme in gluconeogenesis, the metabolic pathway by which the liver synthesizes glucose from 3-carbon precursors. The term FBPase inhibitor refers to compounds that inhibit FBPase enzyme activity and thereby block the conversion of fructose-1,6-bisphosphate, the substrate of the enzyme, to fructose 6-phosphate. FBPase inhibition can be determined directly at the enzyme level by those skilled in the art according to standard methodology (e.g., Gidh-Jain M, Zhang Y, van Poele P D et al., *J Biol Chem.* 1994, 269(44): 27732-8, which is incorporated herein by reference). Alternatively, FBPase inhibition can be assessed according to standard methodology by measuring the inhibition of glucose production by isolated hepatocytes or in a perfused liver, or by measuring blood glucose lowering in normal or diabetic animals (e.g., Vincent M F, Erion M D, Gruber H E, Van den Berghe, *Diabetologia.* 1996, 39(10): 1148-55; Vincent M F, Marangos P J, Gruber H E, Van den Berghe G, *Diabetes* 1991 40(10):1259-66, all of which are incorporated herein by reference). In some cases, in vivo metabolic activation of a compound may be required to generate the FBPase inhibitor. This class of compounds may be inactive in the enzyme inhibition screen, may or may not be active in hepatocytes, but is active in vivo as evidenced by glucose lowering in the normal, fasted rat and/or in animal models of diabetes.

A variety of FBPase inhibitors are described and referenced below; however, other FBPase inhibitors will be known to those skilled in the art. Gruber et al. U.S. Pat. No. 5,658,889 described the use of inhibitors of the AMP site of FBPase to treat diabetes; WO 98/39344 and U.S. Pat. No. 6,284,748 describe purine inhibitors; WO 98/39343 and U.S. Pat. No. 6,110,903 describe benzothiazole inhibitors to treat diabetes; WO 98/39342 and U.S. Pat. No. 6,054,587 describe indole inhibitors to treat diabetes; and WO 00/14095 and U.S. Pat. No. 6,489,476 describe heteroaromatic phosphonate inhibitors to treat diabetes. Other FBPase inhibitors are described in Wright S W, Carlo A A, Carty M D et al., *J Med Chem.* 2002 45(18):3865-77 and WO 99/47549, all of which are incorporated herein by reference.

The compound described herein can also be used in combination with sulfonylureas such as arnaryl, alyburide, glucotrol, chlorpropamide, diabinese, tolazamide, tolinase, acetohexamide, glipizide, tolbutamide, orinase, glimepiride, DiaBeta, micronase, glibenclamide, and gliclazide.

The compound described herein can also be used in combination with antihypertensive agents. Any anti-hypertensive agent can be used as the second agent in such combinations. Examples of presently marketed products containing antihypertensive agents include calcium channel blockers, such as Cardizem, Adalat, Calan, Cardene, Covera, Dilacor, DynaCirc, Procardia XL, Sular, Tiazac, Vascor, Verelan, Isoptin, Ninotop, Norvasc, and Plendil; angiotensin converting enzyme (ACE) inhibitors, such as Accupril, Altace, Captopril, Lotensin, Mavik, Monopril, Prinivil, Univasc, Vasotec and Zestril.

Examples of compounds that may be used in combination with the compound described herein to prevent or treat osteoporosis include: anti-resorptive agents including progestins, polyphosphonates, bisphosphonate(s), estrogen agonists/antagonists, estrogen, estrogen/progestin combinations, Premarin, estrone, estriol or 17.alpha.- or 17.beta.- ethynyl estradiol); progestins including algestone acetophenide, altrenogest, amadinone acetate, anagestone acetate, chlormadinone acetate, cingestol, clogestone acetate, clomegestone acetate, dehnadinone acetate, desogestrel, dimethisterone, dydrogesterone, ethynerone, ethynodiol diacetate, etonogestrel, fluorogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol; and bone resorption inhibiting polyphosphonates including polyphosphonates such as of the type disclosed in U.S. Pat. No. 3,683,080, the disclosure of which is incorporated herein by reference. Examples of polyphosphonates include geminal diphosphonates (also referred to as bis-phosphonates), tiludronate disodium, ibandronic acid, alendronate, resindronate zoledronic acid, 6-amino-1-hydroxy-hexylidene-bisphosphonic acid and 1-hydroxy-3 (methylpentylamino)-propylidene-bisphosphonic acid. Salts, co-crystals and esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl)amino methane diphosphonic acid, butane-4-amino-1-hydroxy-1,1-diphosphonic acid, pentane-5-amino-1-hydroxy-1,1-diphosphonic acid, and hexane-6-amino-1-hydroxy-1,1-diphosphonic acid.

Estrogen agonist/antagonist include 3-(4-(1,2-diphenyl-but-1-e nyl)-phenyl)-acrylic acidr, tamoxifen: (ethanamine, 2-(4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516, the disclosure of which is incorporated herein by reference, 4-hydroxy tamoxifen, which is disclosed in U.S. Pat. No. 4,623,660, the disclosure of which is incorporated herein by reference, raloxifene: (methanone, (6-hydroxy-2-(4-hydroxyphenyl)benzo[b]thien-3-yl)(4-(2-(1-piperidinyl)ethoxy)phenyl)-hydrochloride) which is disclosed in U.S. Pat. No. 4,418,068, the disclosure of which is incorporated herein by reference, toremifene: (ethanamine, 2-(4-(4-chloro-1,2-diphenyl-1-butenyl)phenoxy)-N,N-dimethyl-, (Z)—, 2-hydroxy-1,2,3-propanetricarboxylate (1:1) which is disclosed in U.S. Pat. No. 4,996,225, the disclosure of which is incorporated herein by reference, centchroman: 1-(2-((4-(-methoxy-2,2, dimethyl-3-phenyl-chrornan-4-yl)-phenoxy)-ethyl)-p-pyrrolidine, which is disclosed in U.S. Pat. No. 3,822,287, the disclosure of which is incorporated herein by reference, levormeloxifene, idoxifene: (E)-1-2-(4-(1-(4-iodo-phenyl)-2-phenyl-but-1-enyl)-phenoxy)-ethyl)-pyrro-lidinone, which is disclosed in U.S. Pat. No. 4,839,155, the disclosure of which is incorporated herein by reference, 2-(4-methoxy-phenyl)-3-[4-(2-piperidin-1-yl-ethoxy)-phenoxy]-benzo[b]thio-phen-6-ol which is disclosed in U.S. Pat. No. 5,488,058, the disclosure of which is incorporated herein by reference, 6-(4-hydroxyphenyl)-5-(4-(2-piperidin-1-yl-ethoxy)-benzyl)-naphthalen-2-ol, which is disclosed in U.S. Pat. No. 5,484,795, the disclosure of which is incorporated herein by reference, (4-(2-(2-azabicyclo[2.2.1]hept-2-yl)-ethoxy)-phenyl)-(6-hydroxy-2-(4-hyd-roxy-phenyl)-benzo[b]thiophen-3-yl)-methanone which is disclosed, along with methods of preparation, in PCT publication no. WO 95/10513 assigned to Pfizer Inc, TSE-424 (Wyeth-Ayerst Laboratories) and arazoxifene, cis-6-(4-fluoro-phenyl)-5-(4-(2-piperidin-1-yl-ethoxy)-phenyl)-5,6,-7,8-tetrahydro-naphthalene-2-ol; (−)-cis-6-phenyl-5-(4-(2-pyrrolidin-1-yl-ethoxy)-phenyl)-5,6,7,8-te-trahydro-naphthalene-2-ol (also known as lasofoxifene); cis-6-phenyl-5-(4-(2-pyrrolidin-1-yl-ethoxy)-phenyl)-5,6,7,8-tetrah-ydro-naphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,-4-tetrahydroisoquinoline; cis-6-(4-hydroxyphenyl)-5-(4-(2-piperidin-1-yl-ethoxy)-phenyl)-5,6,-7,8-tetrahydro-naphthalene-2-ol; 1-(4'-pyrrolidinolethoxyphenyl)-2-phenyl-6-hydroxy-1,2,3,4-tetrahydroisoquinoline, 2-phenyl-3-aroyl-benzoth-iophene and 2-phenyl-3-aroylbenzothiophene-1-oxide.

Other anti-osteoporosis agents, which can be used as the second agent in combination with the compound described herein, include, for example, the following: parathyroid hormone (PTH) (a bone anabolic agent); parathyroid hormone (PTH) secretagogues (see, e.g., U.S. Pat. No. 6,132,774), particularly calcium receptor antagonists; calcitonin; and vitamin D and vitamin D analogs. Further anti-osteoporosis agents includes a selective androgen receptor modulator (SARM). Examples of suitable SARMs include compounds such as cyproterone acetate, chlormadinone, flutamide, hydroxyflutamide, bicalutamide, nilutamide, spironolactone, 4-(trifluoromethyl)-2(1H)-pyrrolidino[3,2-g]quinoline derivatives, 1,2-dihydropyridino[5,6-g]quinoline derivatives and piperidino[3,2-g]quinolinone derivatives. Other examples include cypterone, also known as (1b,2b)-6-chloro-1,2-dihydro-17-hydroxy-3'-H-cyclopropa[1,2]

pregna-1,4,6-triene-3,20-dione is disclosed in U.S. Pat. No. 3,234,093. Chlormadinone, also known as 17-(acetyloxy)-6-chloropregna-4,6-diene-3,20-dione, in its acetate form, acts as an anti-androgen and is disclosed in U.S. Pat. No. 3,485,852. Nilutamide, also known as 5,5-dimethyl-3-[4-nito-3-(trifluoromethyl)phenyl]-2,4-imidazolidinedione and by the trade name Nilandron® is disclosed in U.S. Pat. No. 4,097,578. Flutamide, also known as 2-methyl-N-[4-nitro-3-(trifluoromethyl-1)phenyl]propanamide and the trade name Eulexin® is disclosed in U.S. Pat. No. 3,847,988. Bicalutamide, also known as 4'-cyano-a',a',a'-trifluo-ro-3-(4-fluorophenyl sulfonyl)-2-hydroxy-2-methylpropiono-m-toluidide and the trade name Casodex® is disclosed in EP-100172. The enantiomers of biclutamide are discussed by Tucker and Chesterton, J. Med. Chem. 1988, 31, 885-887. Hydroxyflutamide, a known androgen receptor antagonist in most tissues, has been suggested to function as a SARM for effects on IL-6 production by osteoblasts as disclosed in Hofbauer et al. J. Bone Miner. Res. 1999, 14, 1330-1337. Additional SARMs have been disclosed in U.S. Pat. No. 6,017,924; WO 01/16108, WO 01/16133, WO 01/16139, WO 02/00617, WO 02/16310, U.S. Patent Application Publication No. US 2002/0099096, U.S. Patent Application Publication No. US 2003/0022868, WO 03/011302 and WO 03/011824. All of the above references are hereby incorporated by reference herein.

The following examples will further describe the present invention, and are used for the purposes of illustration only, and should not be considered as limiting.

EXAMPLES

Example 1. Preparation of Compound I

An eight-step synthesis of Compound I (five linear steps) suitable for large scale has been developed. The synthesis scheme is shown in Scheme 1 below.

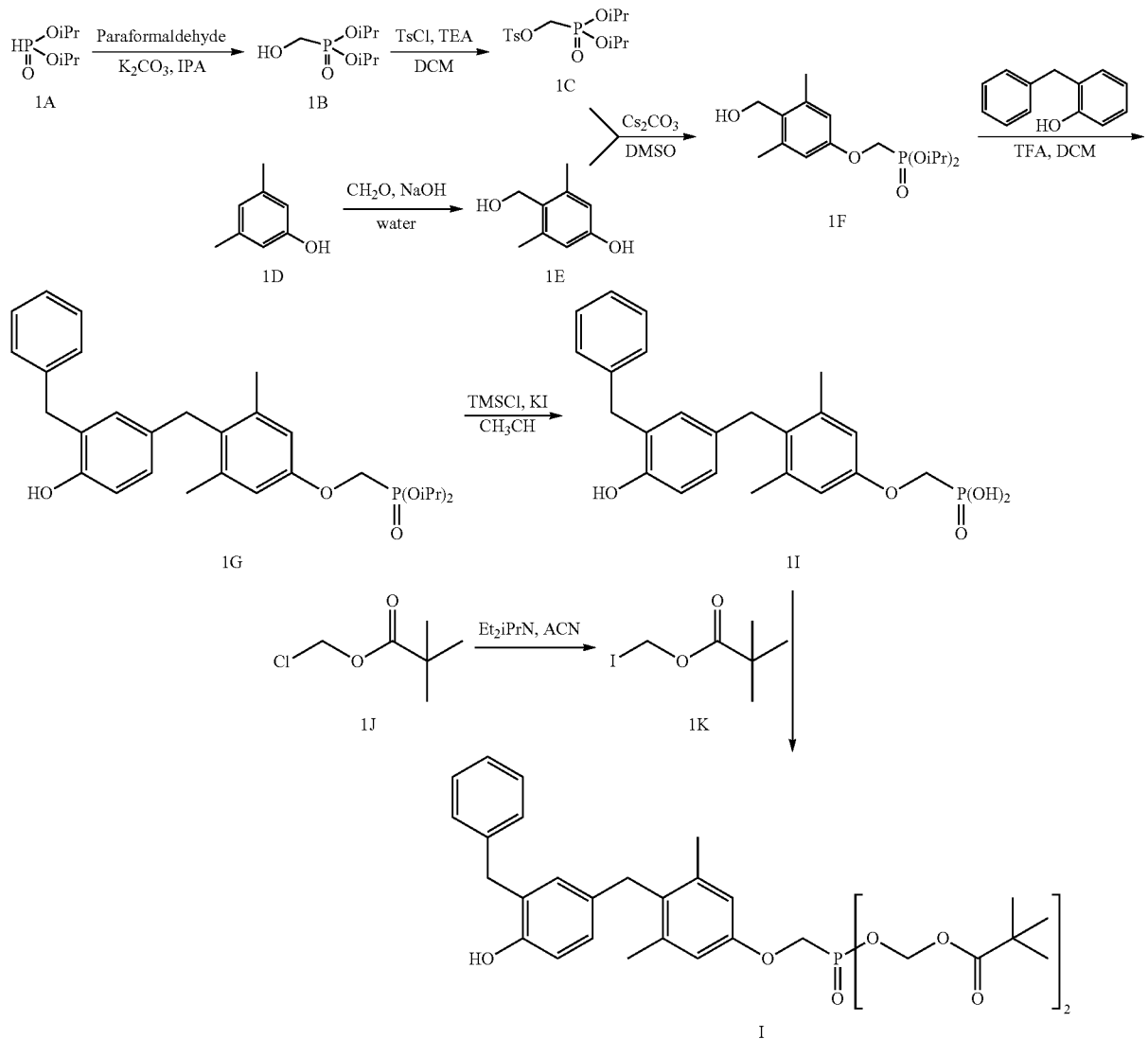

SCHEME 1

A 12 L flask was equipped with an overhead stirrer, heating mantle, temperature probe, condenser with a nitrogen bubbler on the outlet, and an addition funnel. The flask was charged with paraformaldehyde (488 g, 16.3 mol), potassium carbonate (94 g, 0.7 mol), and 2-propanol (4.5 L). The mixture was heated to 50° C. then the heating mantle was turned off. Diisopropylphosphite (Compound 1A, 2260 g, 13.6 mol) was added from the addition funnel at a rate that would maintain the temperature at 50-60° C. for 2.5 h. The reaction progress was monitored by $^1$HNMR. The mixture was cooled to 35° C. over 2 h then filtered through Celite. The pad was washed with 2-propanol (2×200 mL). The mixture was concentrated under reduced pressure. The colorless residual oil (2950 g) was dissolved in dichloromethane (9 L). The solution was washed with 1N HCl (1.35 L) and saturated aqueous $NaHCO_3$ (2.25 L), and dried over $MgSO_4$ (1 kg). The mixture was filtered through Celite and the pad washed with dichloromethane (2×500 mL). The filtrate was concentrated under reduced pressure, giving compound 1B as a colorless oil weighing 2836 g (98% purity).

A 22 L, four-neck flask was equipped with an overhead stirrer, cooling bath, temperature probe, 2 L addition funnel, and a nitrogen bubbler. The flask was charged with Compound 1B (1408 g, 6.67 mol), triethylamine (1350 g, 13.34 mol), and dichloromethane (4 L). The resulting solution was cooled to 5° C. using an ice/water bath. A solution of p-toluenesulfonyl chloride (1335 g, 7.0 mol) in dichloromethane (10 L) was added from the addition funnel at a rate that would keep the temperature below 10° C. for 3 h. The mixture was stirred in an ice bath for 1.75 h, then at ambient temperature (~20° C.) for 15 h. The reaction progress was monitored by $^1$HNMR. The reaction mixture was washed with 1N HCl (6 L) followed by saturated aqueous $NaHCO_3$ (6 L). The organic layer was dried over $MgSO_4$ (400 g) and filtered. The filtrate was concentrated under reduced pressure to give the tosylate Compound 1C as a yellow oil weighing 2111 g (90% yield).

A 50 L, 4-neck flask was equipped with an overhead stirrer, temperature probe, and cooling bath. The flask was charged with 3,5-dimethylphenol (Compound 1D, 2497 g, 20.5 mol), water (14 L), and 50% (wt/wt) aqueous sodium hydroxide (1636 g, 20.5 mol). The mixture was stirred 1.5 h to complete dissolution. The mixture was cooled to 4° C. using an ice/water bath. Formaldehyde (1496 g, 18.5 mol) solution was added in one portion. The mixture was stirred cold throughout the daytime and allowed to warm slowly overnight. The reaction progress was monitored by HPLC. The reaction mixture was diluted with dichloromethane (5 L) and ethyl acetate (5 L). Concentrated HCl was added (1.5 L, 18.0 mol) over 30 minutes to pH 5. After stirring for 6 h, the solid was collected by filtration. The filter cake was washed with water (1.2 L) and dichloromethane (2 L). The beige solid was dried in a vacuum oven (50° C., −30 mmHg) to a constant weight, giving 1222 g (39% yield) of the benzyl alcohol Compound 1E.

A 22 L, four-neck flask was equipped with an overhead stirrer, temperature probe, heating mantle, and condenser with a nitrogen bubbler on the outlet. The flask was charged with the tosylate Compound 1C (2054 g, 5.45 mol), DMSO (2 L), the benzyl alcohol Compound 1E (928 g, 5.62 mol), cesium carbonate (2841 g, 8.72 mol), and DMSO (2.5 L). The mixture was heated to 55° C. over 2 h and maintained at 50-60° C. for 6 h. The reaction progress was monitored by HPLC. The reaction mixture was cooled to 20° C. overnight then cooled to 5° C. (ice/water bath). Ethyl acetate (3.6 L) was added followed by slow addition of 1% (wt/vol) aqueous NaCl solution (7.2 L). The phases were separated and the aqueous layer was extracted with ethyl acetate (2.7 L).

The combined organic layers were washed with brine (2×2.7 L), dried over $MgSO_4$ (500 g), and filtered, rinsing with ethyl acetate (500 mL). The filtrate was concentrated under reduced pressure, obtaining Compound 1F as a thick, dark amber syrup weighing 1935 g.

A 500 mL round-bottom flask was charged with Compound 1F (28.0 g, 84.8 mmol), dichloromethane (200 mL), and 2-benzylphenol (31.23 g, 169.6 mmol). The solution was cooled to −1° C. using an ice/MeOH bath. Trifluoroacetic acid (18.9 mL, 254.4 mmol) was added from an addition funnel over 1 minute. The reaction progress was monitored by HPLC. The reaction mixture was poured into water (200 mL) and the mixture was stirred for 5 minutes. The phases were separated and the organic layer was washed with water (200 mL). The organic layer was dried over $MgSO_4$, filtered, and concentrated to a thick, brown oil. Ether (200 mL) was added and the mixture was stirred at ambient temperature (~18° C.). After 10 seconds, solids started to form and the mixture thickened quickly. After stirring at room temperature for 18 h, the solid was collected by filtration and washed with ether (50 mL). The white solid was dried under high vacuum giving 30.34 g of Compound 1G (72% yield).

A 250 mL round-bottom flask was charged with the diisopropyl ester Compound 1G (29.33 g, 59.1 mmol), potassium iodide (31.38 g, 189.12 mmol), acetonitrile (120 mL), and chlorotrimethylsilane (24.0 mL, 189.12 mmol). The resulting suspension was heated at 50° C. The reaction progress was monitored by HPLC. The mixture was cooled to 25° C. Water (120 mL) was added, the mixture was stirred 5 min, and the layers were separated. The aqueous layer was extracted with ethyl acetate (60 mL). The combined organic layers were washed with brine (60 mL), dried over magnesium sulfate, filtered and concentrated to dryness to give a thick oil Compound 1I. Upon standing, this material solidified to a tan solid, which was ground into a fine powder and stirred vigorously with 25 mL of water at 35-40° C. for 30 minutes. The tan solids were filtered, rinsed with a small portion of water and dried on a lyophilizer overnight.

Sodium iodide (398.1 g, 2.49 mol) was added to acetone (850 mL) in a 2 L round-bottom flask at room temperature. After cooling to room temperature, chloromethyl pivalate Compound 1J (250 g, 1.66 mol) was added in one portion and the reaction mixture became turbid. The white slurry was stirred at room temperature overnight. The salts were filtered off and rinsed with acetone (100 mL). The combined brown filtrates were concentrated to dryness to give a brown slurry which was taken up in ether (500 mL). The solids were filtered off and rinsed with ether (100 mL). The combined filtrates were concentrated to dryness to give crude iodomethyl pivalate Compound 1K which was used without purification.

Diethylisopropylamine (19.5 mL, 118.2 mmol) was added to a solution of crude phosphonic acid Compound 1I (59.1 mmol) in acetonitrile at room temperature (300 mL). The orange turbid mixture was heated at 40° C. and crude iodomethyl pivalate Compound 1K (28.6 g, 118.2 mmol) was added. The reaction was monitored by HPLC. After 3.5 h, additional crude iodomethyl pivalate Compound 1K (14.3 g, 59.1 mmol) and diethylisopropylamine (9.75 mL, 59.1 mmol) were added. The reaction mixture was stirred at 40° C. overnight. A final aliquot of crude iodomethyl pivalate Compound 1K (14.3 g, 59.1 mmol) and diethylisopropylamine (9.75 mL, 59.1 mmol) were added. After stirring for an additional 2 h, the cooled reaction mixture was poured into a mixture of ethyl acetate (150 mL) and water (300 mL). The layers were separated and the organics were washed sequentially with water (150 mL), a saturated solution of sodium bicarbonate (100 mL), and brine (100 mL) then dried (MgSO$_4$), filtered and concentrated to dryness to a brown oil. The residue was taken up in 1/1 acetone/hexanes (400 mL) and filtered through a pad of silica. The pad was rinsed with 1/1 acetone/hexanes (100 mL). The orange filtrate was concentrated to dryness and the orange oil was taken up in acetone (60 mL). Hexanes (300 mL) were added and the cloudy solution was stirred at room temperature. After a few minutes, a solid appeared and the mixture turned slowly into a thick slurry. After stirring at room temperature overnight, the tan solid was collected by filtration, rinsed with 1/6 acetone/hexanes (100 mL), air dried, and then dried under high vacuum to give an off white solid Compound I (24.06 g, 68.7% yield).

Example 2. Effects of Single Oral Doses on Plasma Cholesterol Levels

Compound I was tested to determine the cholesterol lowering efficacy and potency of Compound I following oral administration of single dose to a standard rodent model of hypercholesterolemia, the cholesterol-fed Sprague Dawley rat.

Male Sprague Dawley rats were obtained from Harlan (Livermore, Calif.) at a body weight of 250 g, caged 3 rats/cage, and housed under a 12 h:12 h, light:dark cycle (lights on at 7 AM). Pelleted 5001 chow containing 1.5% cholesterol and 0.5% cholic acid (Harlan Teklad, Indianapolis, Ind.) was provided for 2 weeks prior to the initiation of treatment. Food and water were provided ad libitum.

Compound I was dissolved in 100% PEG-400. T3 was dissolved in 100% PEG-400 (protocol 1) or in 100% PBS (protocol 2). All formulations were prepared just prior to initiation of treatment.

Male Sprague Dawley rats (~250 g) were fed a diet containing 1.5% cholesterol and 0.5% cholic acid for 2 weeks prior to the initiation of treatment. Compound I was administered as an oral solution in PEG-400 and phosphate buffered saline, respectively, at doses ranging from 0.3 to 100 mg/kg Compound I. Thyroid hormone T3 (0.1 mg/kg) was evaluated as a positive control.

A small blood sample was obtained from each rat by means of a small incision in the tail vein prior to treatment. The blood sample was collected in a tube containing lithium heparin. Animals (6/group) were dosed by gavage according to the schedule shown in the Table 1 below:

TABLE 1

Dosing schedule for Protocol 1

| Route | Compound | # of animals | Dose concentration | Dose Solution (mg/ml) | Dose Solution (mg/ml) |
|---|---|---|---|---|---|
| PO | Compound I | 6 | 100 | 50 | 2 |
| PO | Compound I | 6 | 30 | 15 | 2 |
| PO | Compound I | 6 | 10 | 5 | 2 |
| PO | Compound I | 6 | 3 | 1.5 | 2 |
| PO | Compound I | 6 | 1 | 0.5 | 2 |
| PO | Compound I | 6 | 0.3 | 0.15 | 2 |
| PO | Vehicle (PEG-400) | 6 | NA | NA | 2 |
| PO | T3 | 6 | 0.1 | 0.1 | 1 |

At 24 hours after dose administration, a second blood sample was taken as described above.

Analysis of Plasma Cholesterol:

Plasma was prepared from the blood samples by centrifugation in an Eppendorf Microfuge (14,000 rpm, 2 min, room temperature). Total plasma cholesterol was measured using the Infinity cholesterol reagent (Thermo Electron Corporation, Waltham, Mass.) and a standard curve prepared with a 300 mg/dL cholesterol standard. Plasma cholesterol levels were measured at baseline and 24 hours after treatment using the Infinity cholesterol reagent.

Figure 2:
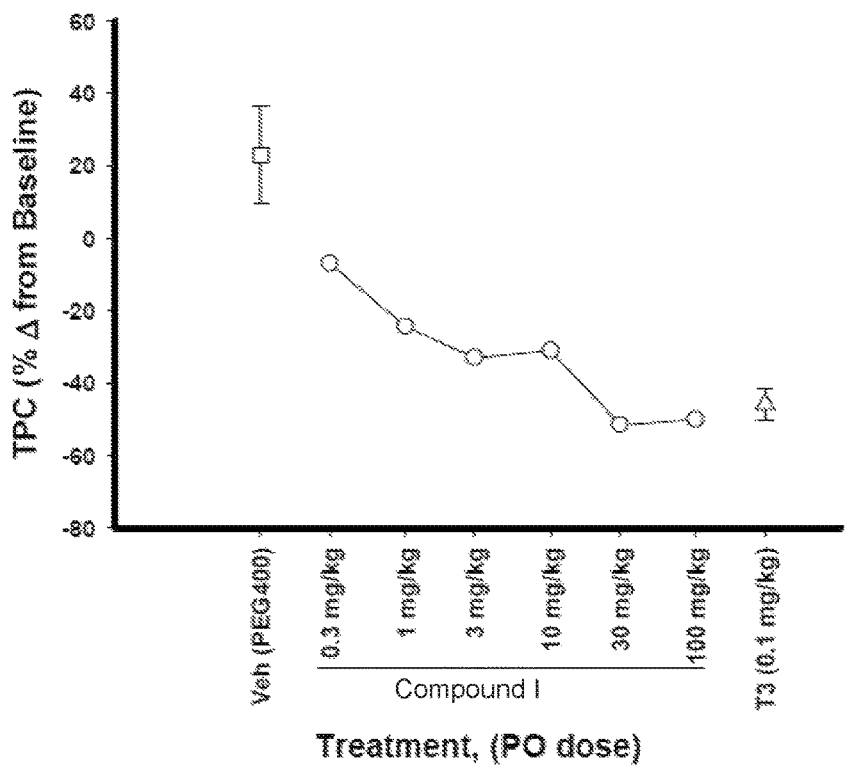
FIG. 2 shows the percentage change in in total plasma cholesterol (TPC) levels from baseline values at 24 hours after administration of Compound I to male, cholesterol-fed Sprague Dawley rats (n=6/group).
Figure 3:
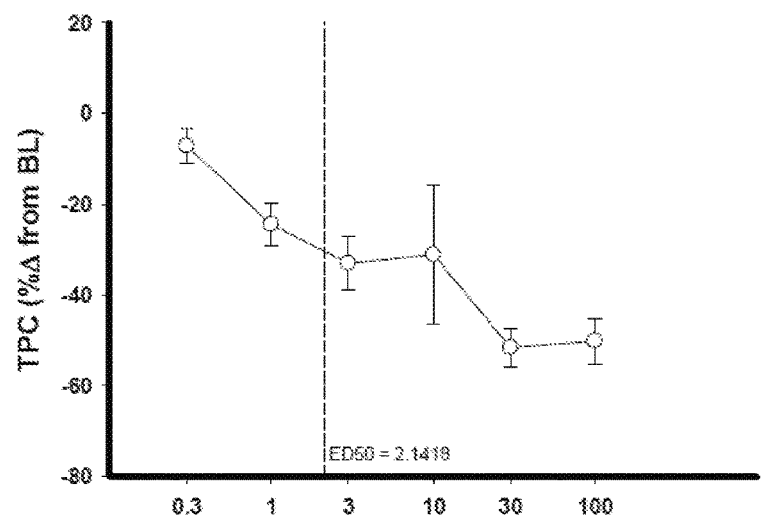
FIG. 3 shows the $ED_{50}$ value, defined as the dose that elicits a half-maximal reduction in total plasma cholesterol (TPC) levels from baseline, of Compound I.

FIG. 1 shows the total plasma cholesterol levels (mean±SEM) in male, cholesterol-fed Sprague Dawley rats (n=6/group) at baseline and at 24 hours after administration of vehicle or Compound I. FIG. 2 shows the percentage change in in total plasma cholesterol (TPC) levels from baseline values at 24 hours after administration of compound I to male, cholesterol-fed Sprague Dawley rats (n=6/group). FIG. 3 shows the ED$_{50}$ value, defined as the dose that elicits a half-maximal reduction in total plasma cholesterol (TPC) levels from baseline, of Compound I. As shown in FIGS. 1 and 2, oral administration of Compound I resulted in dose dependent reductions of plasma cholesterol levels up to about 120 mg/dL (FIG. 1) or about 50% (FIG. 2) relative to baseline levels. The reduction in cholesterol levels was similar at the two highest doses, 30 and 100 mg/kg, indicating that the ~120 mg/dL or ~50% reductions observed at these doses was the maximal response. In FIG. 3, the ED50 value for the cholesterol lowering response was approximately 2 mg/kg. The magnitude of cholesterol lowering at the two highest doses of Compound I was comparable to that of T3 administered at a dose of 0.1 mg/kg (FIG. 1).

Therefore, the single oral administration of Compound I to cholesterol-fed rats resulted in dose-dependent reductions in plasma cholesterol with ED$_{50}$ values of about 2 mg/kg.

Example 3. Effects on Plasma Cholesterol Levels and Thyroid Function Indicators

The effects of once-daily oral administration of Compound I on plasma cholesterol levels and thyroid function indicators in beagle dogs were evaluated for 14 days.

Male and female beagle dogs were purchased from Marshall Farms (North Rose, N.Y.) at approximately 9-15 kg in body weight. Animals were housed individually under a 12 hour lighting cycle (7 am-7 pm light) and controlled temperature (~22° C.). The dogs were fed twice-daily with Teklad 8563 chow (Harlan Teklad, Madison, Wis.) and allowed water ad libitum.

Compound I was dissolved in 100% PEG-400. The formulation was prepared just prior to initiation of treatment and stored at 4° C. A fresh formulation was prepared for each 7 day treatment period.

Twelve beagle dogs (9-15 kg) were randomized into 6 dosing groups (1 male and 1 female/group) and gavaged once-daily with a PEG-400 solution of Compound I at doses of 0.1, 0.3, 1, 3, or 10 mg/kg or with vehicle for 14 days. At the end of the treatment cycle (Cycle 1), the dogs were washed out for 6 weeks and then entered into a second 14-day treatment cycle. Cycle 2 employed the same dosing paradigm as Cycle 1, but animals were randomized to Cycle 2 in such a way that the combined dosing groups from the two cycles each consisted of 4 different animals (2 males, 2 females). Blood samples were collected at baseline and appropriate time intervals thereafter and analyzed for total plasma cholesterol levels, serum levels of total T4 (tT4), free T4 (fT4), total T3 (tT3), free T3 (fT3), thyroid stimulating hormone (TSH), and plasma drug levels.

Plasma Cholesterol:

Total plasma cholesterol was measured using an Infinity cholesterol reagent (Thermo Electron Corporation, Waltham, Mass.) and with use of a standard curve prepared from a 300 mg/dL cholesterol standard. Average values±the standard error of the mean (SEM) were calculated for all treatment groups.

Thyroid Function Tests (TFTs).

Serum samples were shipped on dry ice to the Diagnostic Center for Population and Animal Health (Lansing, Mich.) and assayed for total T4 (tT4), free T4 (fT4), total T3 (tT3), free T3 (fT3), and thyroid stimulating hormone (TSH). Average values±the standard error of the mean (SEM) were calculated for all treatment groups.

Figure 4:
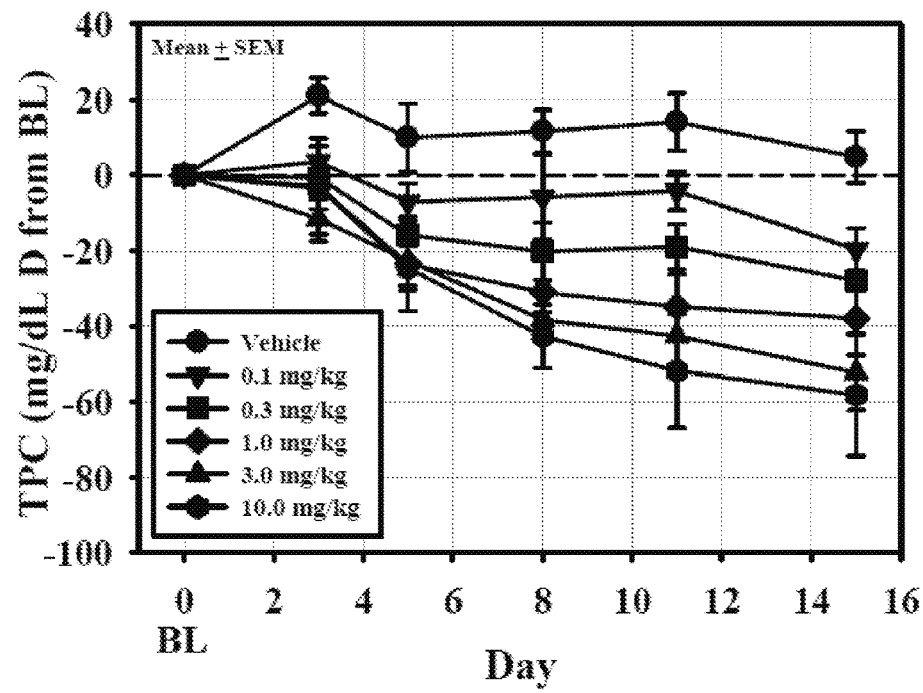
FIG. 4 shows the effect of once-daily oral administration of Compound I on total plasma cholesterol (TPC) levels in beagle dogs expressed as change in levels, mg/dL, from baseline.
Figure 5:
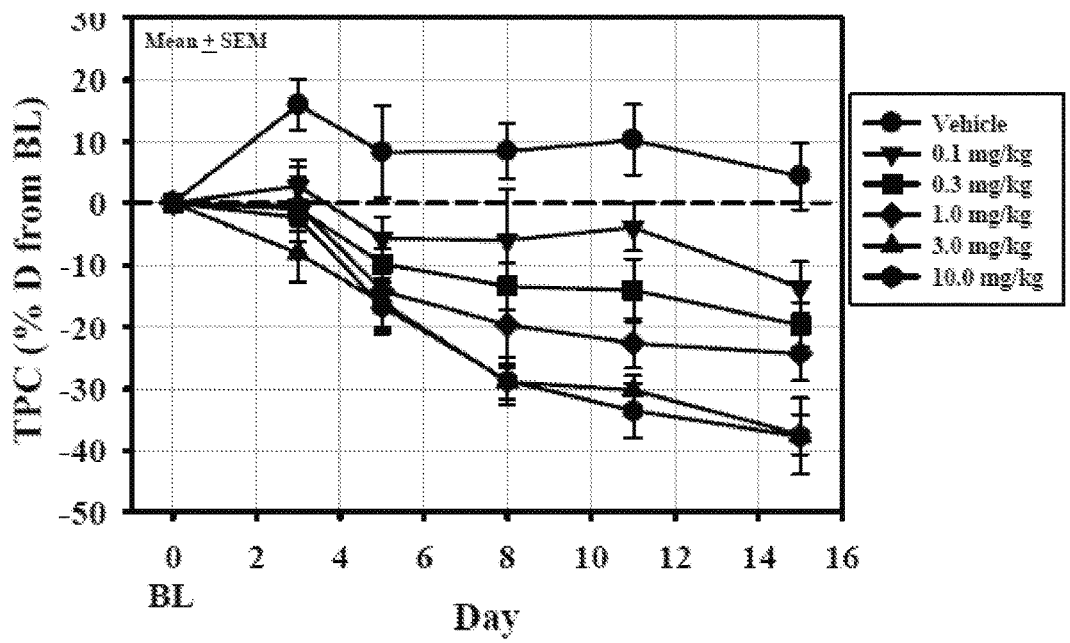
FIG. 5 shows the effect of once-daily oral administration of Compound I on total plasma cholesterol (TPC) levels in beagle dogs (n=4/group) expressed as % change from baseline.

Average values of total plasma cholesterol levels at baseline in the various treatment groups ranged from 135.5 to 154.9 mg/dl. FIG. 4 shows the effect of once-daily oral administration of Compound I on total plasma cholesterol (TPC) levels in beagle dogs expressed as change in levels, mg/dL, from baseline. FIG. 5 shows the effect of once-daily oral administration of Compound I on total plasma cholesterol (TPC) levels in beagle dogs (n=4/group) expressed as % change from baseline. As shown in FIGS. 4 and 5, the once-daily administration of Compound I resulted in a progressive, dose dependent reduction of total plasma cholesterol levels from baseline, with an average reduction on Day 15 of about 20 mg/dL or about 15% from baseline at the lowest dose evaluated (0.1 mg/kg/day), and of about 60 mg/dL or about 38% from baseline at the highest dose evaluated (10 mg/kg/day).

Figure 6:
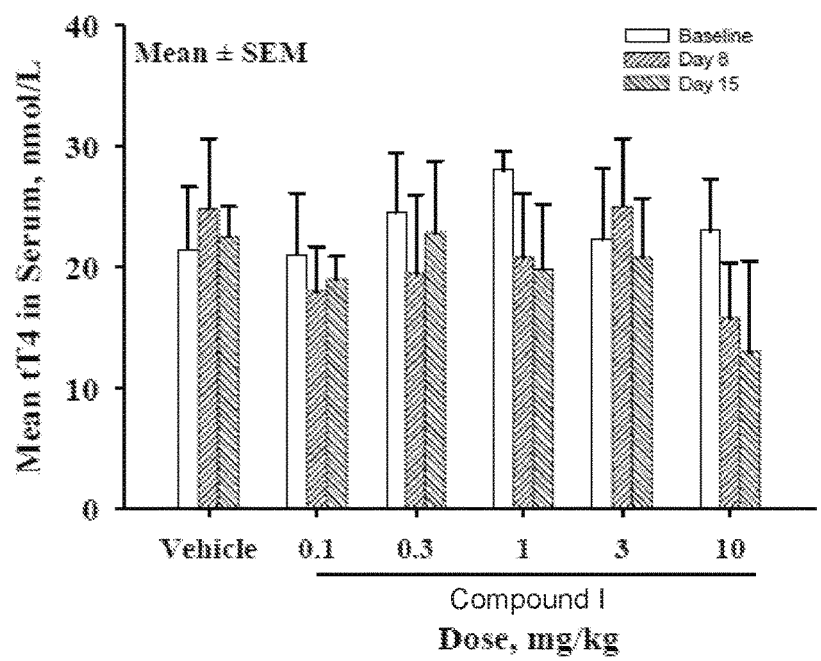
FIG. 6 shows the tT4 levels in serum after once-daily oral administration of Compound I to beagle dogs for 14 days.

FIG. 6 shows the tT4 levels in serum after once-daily oral administration of Compound I to beagle dogs for 14 days. In FIG. 6, the reductions of 6.7-9.5% from baseline were observed on Day 15 in the groups treated with doses of 0.1, 0.3, and 3 mg/kg/day of Compound I. In the groups treated with 1 and 10 mg/kg/day of Compound I, tT4 levels were reduced by about 29% and about 44%, respectively on Day 15 relative to baseline. A small increase of tT4 levels from baseline (about 5%) was observed in the vehicle treated group on Day 15.

Figure 7:
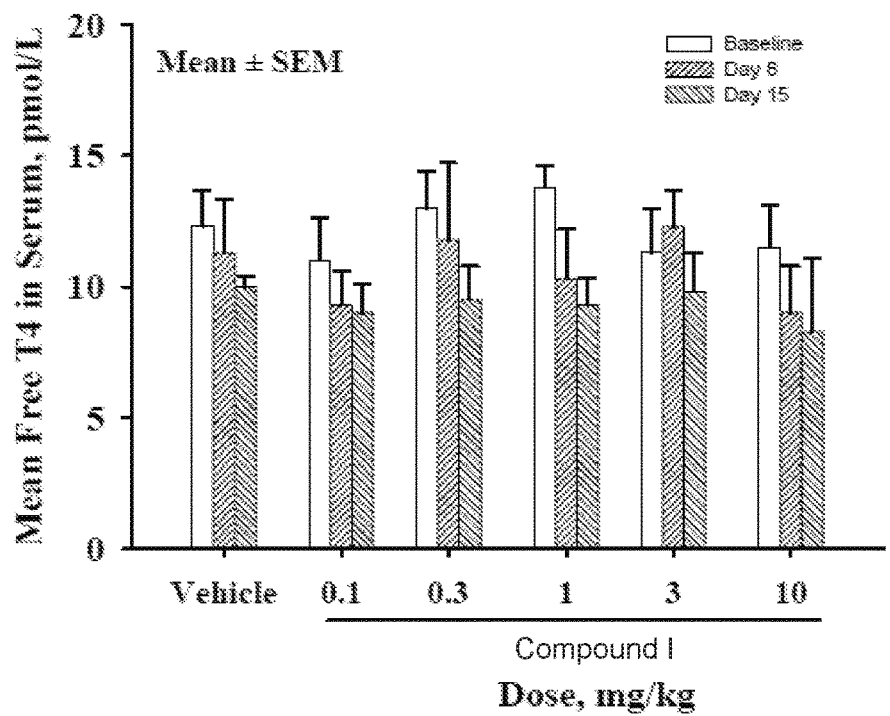
FIG. 7 shows the fT4 levels in serum after once-daily oral administration of Compound I to beagle dogs for 14 days.

FIG. 7 shows the fT4 levels in serum after once-daily oral administration of Compound I to beagle dogs for 14 days. In FIG. 7, the reductions of about 13-32% from baseline were observed in the Compound I treated groups on Day 15. However, the changes were not dose dependent. Moreover, about 19% reduction in fT4 levels from baseline was observed in the vehicle-treated group on Day 15.

Figure 8:
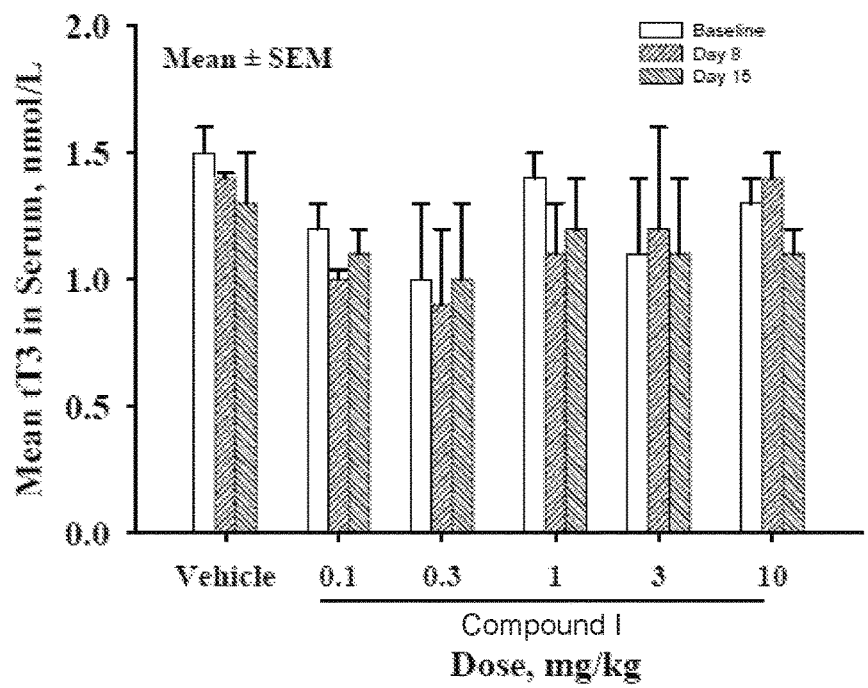
FIG. 8 shows the tT3 levels in serum after once-daily oral administration of Compound I to beagle dogs for 14 days.

FIG. 8 shows the tT3 levels in serum after once-daily oral administration of Compound I to beagle dogs for 14 days. In FIG. 8, reductions of about 8-15% were observed on Day 15 relative to baseline in the treatment groups. However, the reductions were not dose dependent. Moreover, about 13% reduction in tT3 levels from baseline was observed in the vehicle-treated group on Day 15.

Figure 9:
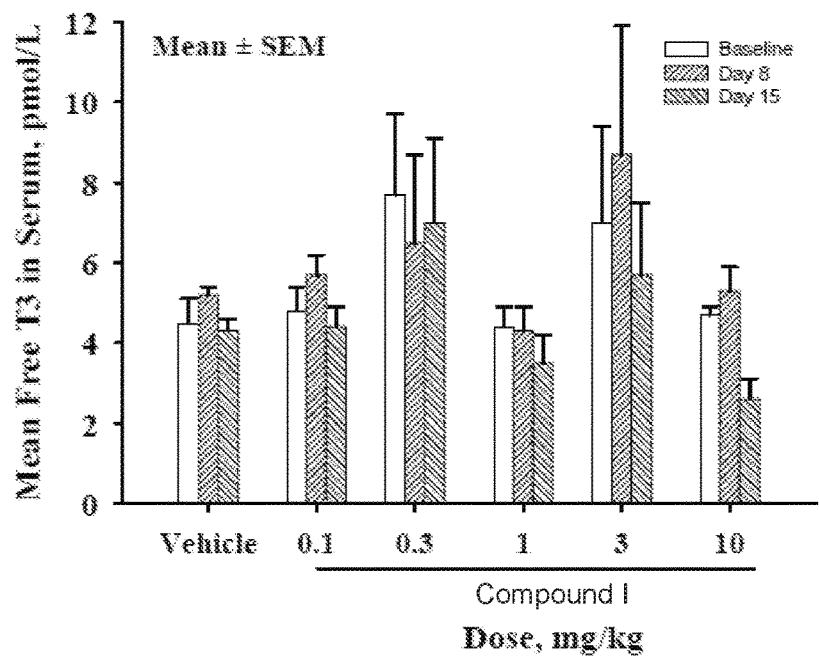
FIG. 9 shows the fT3 levels in serum after once-daily oral administration of Compound I to beagle dogs for 14 days.

FIG. 9 shows the fT3 levels in serum after once-daily oral administration of Compound I to beagle dogs for 14 days. In FIG. 9, the reductions of about 8-20% from baseline were observed on Day 15 in the groups treated with doses up to and including 3 mg/kg/day of compound I. In the group treated with 10 mg/kg/day of Compound I, tT4 levels were reduced by ~45% on Day 15 relative to baseline values. About 4% reduction of fT3 levels from baseline was observed in the vehicle-treated group on Day 15.

Figure 10:
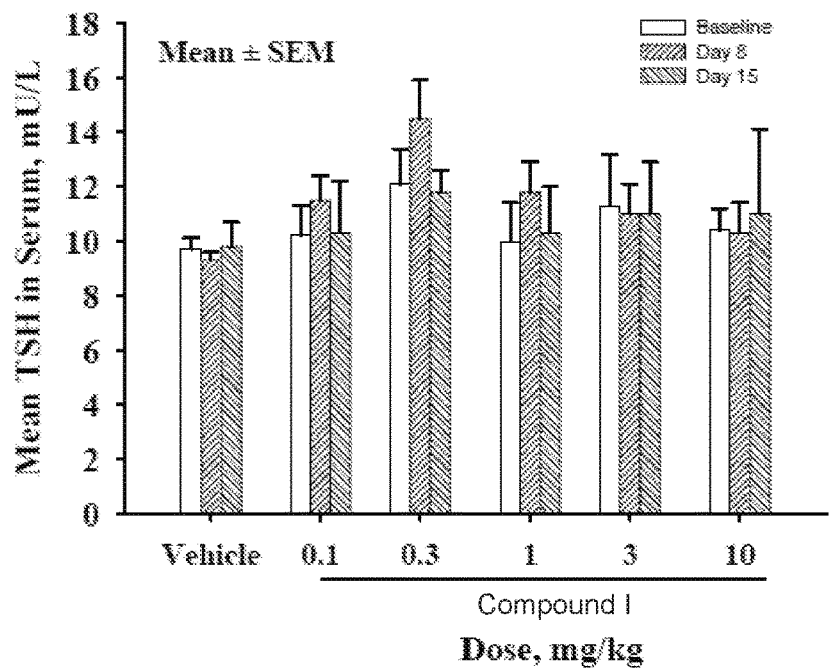
FIG. 10 shows the TSH serum levels after once-daily oral administration of Compound I to beagle dogs for 14 days.

FIG. 10 shows TSH levels in serum after once-daily oral administration of Compound I to beagle dogs for 14 days. In FIG. 10, no meaningful changes from baseline values were observed in any of the treatment groups on Day 15. Administration of Compound I (0.1 mg/kg/day to 10 mg/kg/day) did not show any effect on the TSH level in the dog serum.

Therefore, the once-daily oral treatment of beagle dogs for 14 days with Compound I (0.1-10 mg/kg/day) reduced total plasma cholesterol levels in a dose dependent manner by 15-38%. Serum TSH levels were essentially unaffected by treatment with Compound I. Other indicators of thyroid function in general did not undergo major changes except in the highest dose group (10 mg/kg/day) at which about 45% reductions in tT4 and fT3 were observed.

Example 4. Effect of Compound 1 on Free 3,5,3'-Triiodothyronine (fT3) and Free 3,5,3',5' Tetraiodothyronine (fT4) Levels Compound I was tested to measure its ex vivo effects at concentrations ranging from 0 to 100 µM on the free 3,5,3'-triiodothyronine (fT3) and the free 3,5,3',5' tetraiodothyronine (fT4) levels in human, monkey, dog, and rat sera.

Stock solution of Compound I was prepared in 100% DMSO. The test articles were combined with either human, monkey, dog or rat serum in a microcentrifuge tube at concentrations of 1, 3, 10, 30, and 100 µM, and incubated at 37° C. with agitation (800 rpm) using a Thermomixer R (Eppendorf, Inc.; Westbury, N.Y.) for 1 h. The DMSO concentration in the serum incubations was kept constant at 1%. Following the serum incubations, fT3 and T4 quantification was accomplished using the GammaCoat™ FT3 and the GammaCoat™ FT4 RIA kits, respectively. The kits were used according to the manufacturer's recommendations. The T3 assay specifications indicate 0.2% cross-reactivity with T4, while the T4 assay specifications indicate 0.5% cross-reactivity with T3. In these MA assays, a shaking water bath and a Wallac Wizard 1470 automatic gamma counter (Perkin Elmer, Inc.; Waltham, Mass.) were used. At each concentration tested, a background signal was subtracted from the data. This background signal was determined in samples of the test articles in PBS in the absence of serum. All assays were performed in duplicate.

Figure 11A:
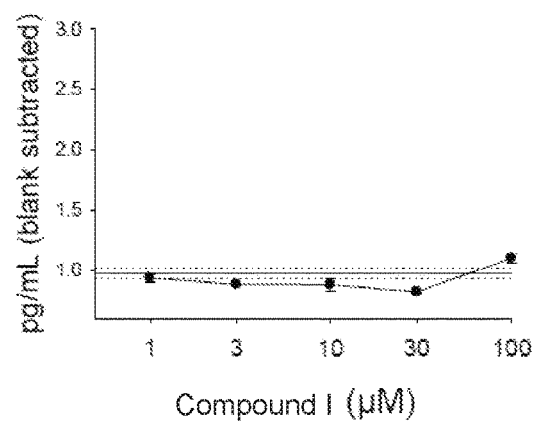
FIGS. 11a and 11b show the effects of Compound I on fT3 and fT4 levels in human serum.
Figure 11B:
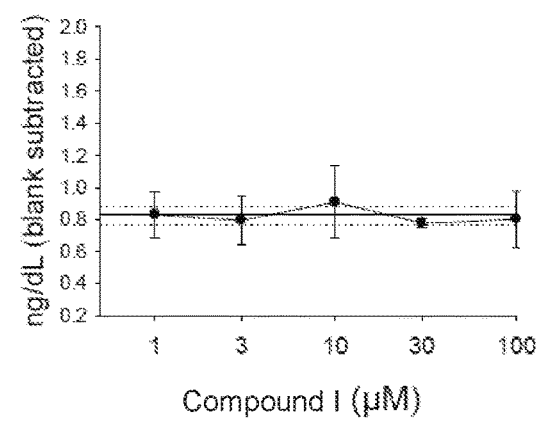
Figure 12A:
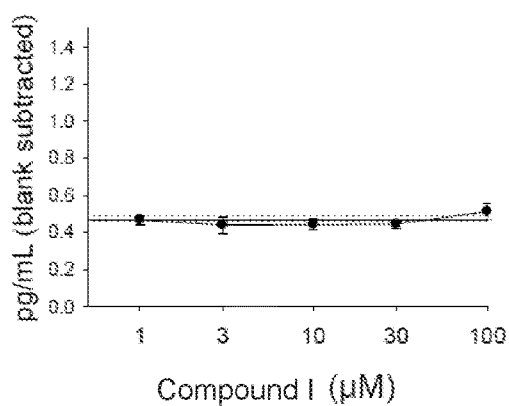
FIGS. 12a and 12b show the effects of Compound I on fT3 and fT4 levels in monkey serum.
Figure 12B:
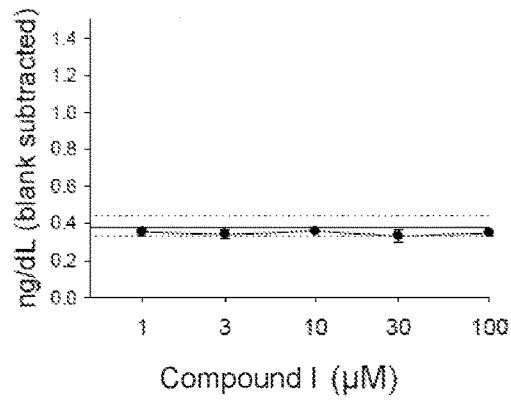
Figure 13A:
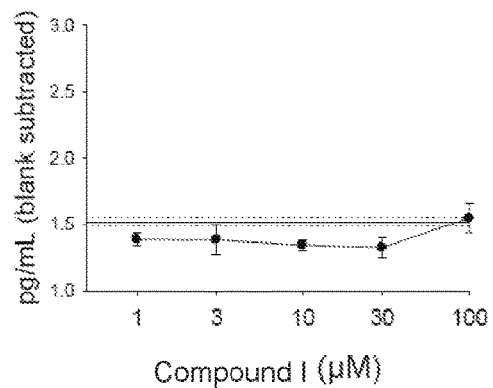
FIGS. 13a and 13b show the effects of Compound I on fT3 and fT4 levels in dog serum.
Figure 13B:
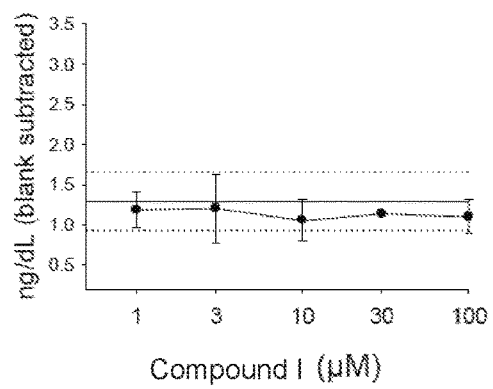
Figure 14A:
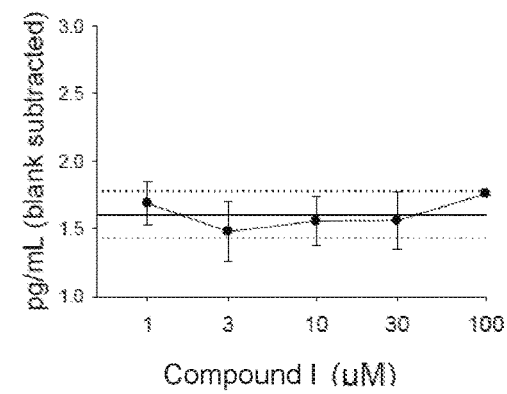
FIGS. 14a and 14b show the effects of Compound I on fT3 and fT4 levels in rat serum.
Figure 14B:
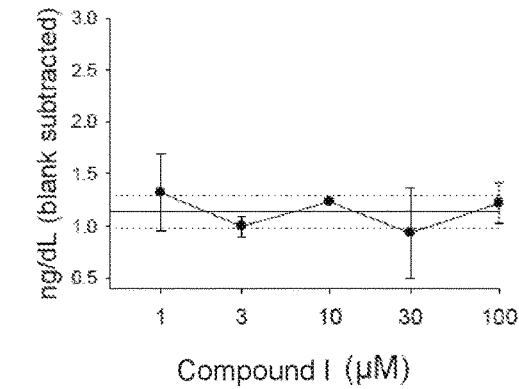

FIGS. 11a and 11b shows the effects of Compound I on fT3 and fT4 levels in human serum. FIGS. 12a and 12b shows the effects of Compound I on fT3 and fT4 levels in monkey serum. FIGS. 13a and 13b shows the effects of Compound I on fT3 and fT4 levels in dog serum. FIGS. 14a and 14b shows the effects of Compound I on fT3 and fT4 levels in rat serum. The solid and dotted straight lines indicate the mean and standard deviation of fT3 or fT4 levels in untreated serum samples containing 1% DMSO. Table 2 summarizes the highest concentrations at which no increases in fT3 or fT4 levels were observed after exposure of human, monkey, dog, or rat serum to Compound I.

TABLE 2

Summary of the highest concentrations at which no increases in fT3 or T4 levels were observed after exposure of human, monkey, dog, or rat serum.

| Test Compound | Human Serum fT3 | Human Serum fT4 | Monkey Serum fT3 | Monkey Serum fT4 | Dog Serum fT3 | Dog Serum fT4 | Rat Serum fT3 | Rat Serum fT4 |
|---|---|---|---|---|---|---|---|---|
| Compound I | 30 µM | 100 µM | 30 µM | 100 µM | 100 µM | 100 µM | 100 µM | 100 µM |

As shown in the table, for the human serum, Compound I showed no effect on fT3 when the concentration was less than 30 and Compound I showed no effect on fT4 when the concentration was less than 100 μM.

Example 5. Comparison of Compound I and Compound MB07811

Compound I was compared with Compound MB07811 with respect to their efficacy in lowering cholesterol and their effects on the total T4 (tT4) and thyroid stimulating hormone (TSH).

Figure 15:
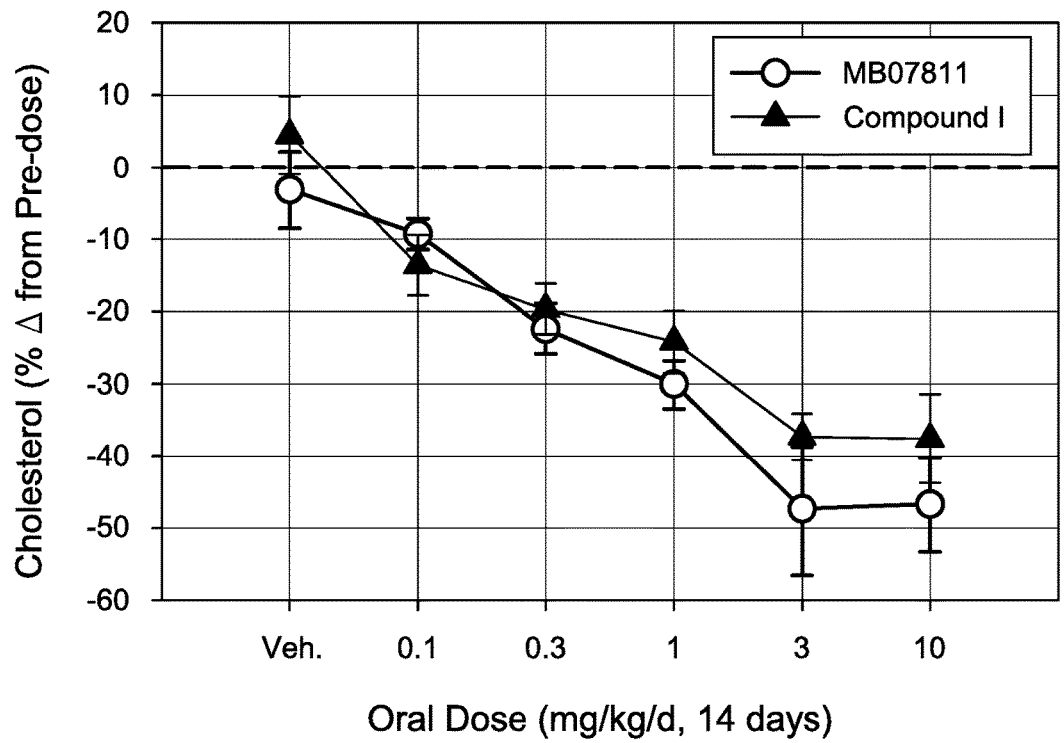
FIG. 15 shows the oral efficacy of Compound I or Compound MB07811 in a comparative study.

FIG. 15 shows the oral efficacy of Compound I and Compound MB07811. In FIG. 15, the two compounds have shown similar oral efficacy in reducing cholesterol level during the 14-day test.

Compound I and Compound MB07811 were tested to determine the effects of oral administration of each compound once-daily for 14 days followed by alternate day dosing for 14 days on plasma cholesterol levels and indicators of thyroid function in beagle dogs.

Male and female Beagle dogs were purchased from Marshall Farms (North Rose, N.Y.) at approximately 9-15 kg. Animals were housed individually under a 12-hour lighting cycle (7 am-7 pm light) and controlled temperature (~22° C.). The dogs were fed twice daily with Teklad 8563 chow (Harlan Teklad, Madison, Wis.) and allowed water ad libitum.

MB07811 was administered as a suspension in 0.5% CMC/1% Lutrol in deionized water. To prepare the vehicle, the required amount of CMC was weighed and dissolved in deionized water using a Waring blender. The required amount of Lutrol F68 was weighed and slowly added to the Waring blender while mixing. The contents of the blender were mixed until dissolved and stored refrigerated. To prepare the dosing formulations, the required amount of MB07811 was weighed into a beaker and the required volume of vehicle slowly added to the beaker while stirring using a magnetic stir bar and stir plate. The contents of the beaker were stirred until a fine paste was obtained. Vehicle was added to the beaker while stirring until a uniform MB07811 suspension was obtained. The formulation was prepared fresh on a weekly basis and stored refrigerated.

Twelve beagle dogs (9-15 kg) were randomized into 6 dosing groups (1 male and 1 female/group) and gavaged once-daily with a 0.5% CMC/1% Lutrol F68 suspension of MB07811 at doses of 0.1, 0.3, 1, 3, or 10 mg/day or with vehicle for 14 days. At the end of the treatment cycle (Cycle 1), the dogs were washed out for 4 weeks and then entered into a second 14-day treatment cycle. Cycle 2 employed the same dosing paradigm as Cycle 1, but animals were randomized to Cycle 2 in such a way that the combined dosing groups from the two cycles consisted of 4 different animals (2 males, 2 females) each. At the conclusion of Cycle 2, dosing was continued on alternate days for an additional 14-day period (Cycle 2 Extension). Blood samples were collected at baseline and appropriate time intervals thereafter and analyzed for total plasma cholesterol levels, serum levels of total T4 (tT4), free T4 (fT4), total T3 (tT3), free T3 (fT3), and thyroid stimulating hormone (TSH).

Compound I was dissolved in 100% PEG-400. The formulation was prepared just prior to initiation of treatment and stored at 4° C. A fresh formulation was prepared for each 7-day treatment period.

Figure 16A:
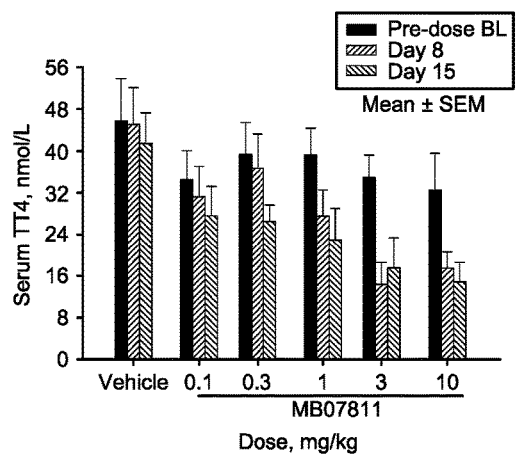
FIGS. 16a and 16b shows the average tT4 levels in the animal serum when treated with compound I or compound MB07811 at various doses.
Figure 16B:
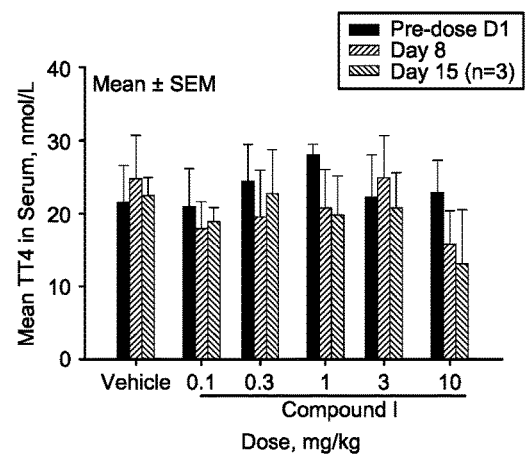
Figure 17A:
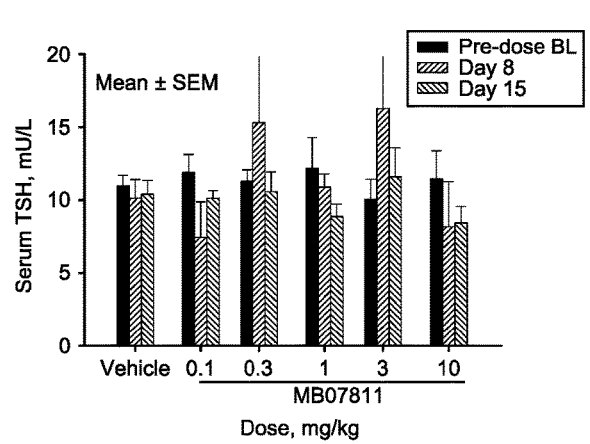
FIGS. 17a and 17b shows the serum Thyroid stimulating hormone (TSH) levels when treated with compound I or compound MB07811 at various doses.
Figure 17B:
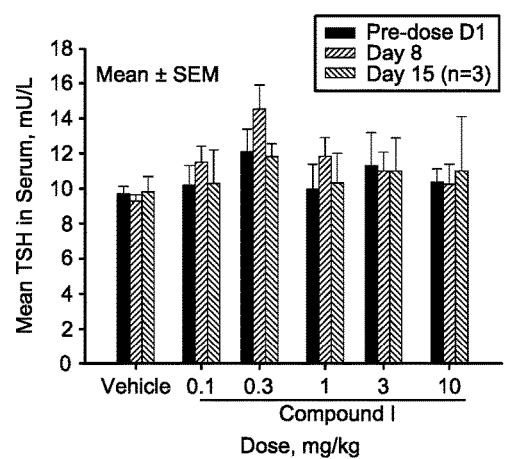

Twelve beagle dogs (9-15 kg) were randomized into 6 dosing groups (1 male and 1 female/group) and gavaged once-daily with a PEG-400 solution of Compound I at doses of 0.1, 0.3, 1, 3, or 10 mg/kg or with vehicle for 14 days. At the end of the treatment cycle (Cycle 1), the dogs were washed out for 6 weeks and then entered into a second 14-day treatment cycle. Cycle 2 employed the same dosing paradigm as Cycle 1, but animals were randomized to Cycle 2 in such a way that the combined dosing groups from the two cycles each consisted of 4 different animals (2 males, 2 females). Blood samples were collected at baseline and appropriate time intervals thereafter and analyzed for total plasma cholesterol levels, serum levels of total T4 (tT4), free T4 (fT4), total T3 (tT3), free T3 (fT3), and thyroid stimulating hormone (TSH), and for plasma drug levels FIG. 16a and FIG. 16b show the average tT4 levels in the animal serum when treated with compound MB07811 and compound I respectively at various doses. Samples were collected at pre-dose as baseline, at 8-day, and 15-day post administration. As shown in FIGS. 16a and 16b, Compound I shows a reduced effect on T4 levels at all five doses (0.1 mg/kg, 0.3 mg/kg, 1 mg/kg, 3 mg/kg, and 10 mg/kg) when compared with Compound I. FIG. 17a and FIG. 17b show the serum TSH levels when treated with compound I and compound MB07811 respectively at various doses. Samples were collected at pre-dose as baseline, at 8-day, and 15-day post administration. As shown in FIGS. 17a and 17b, Compound I shows no effect on the TSH level at all five doses (0.1 mg/kg, 0.3 mg/kg, 1 mg/kg, 3 mg/kg, and 10 mg/kg) when compared with compound MB07811.

Therefore, Compound I has similar cholesterol lowering activity as Compound MB07811 but it has a much reduced effect on the thyroid hormone axis (T4 and TSH) than Compound MB07811.

Example 5. Safety Study of Compound I

A pilot rat 28-day study was conducted using Compound I to test its safety. Two doses were tested, 1 mg/kg per day and 5 mg/kg per day. The control group was not injected with Compound I during the study. The mice were sacrificed on day 29 and then analyzed for clinical signs, BW, FC Clinical pathology (including TSH, T3, T4), gross pathology, organ weights, histopathology, toxicokinetics.

At both dose levels, the study results showed that no deaths or adverse effects on body weight, food consumption, hematology, serum chemistry or urinalysis, or macroscopic or microscopic pathology. There was also no evidence of cardiac or liver necrosis, or TFT effects greater than Compound MB07811.

What is claimed is:
1. A method comprising:
(a) reacting a compound of (I-A)

I-A with paraformaldehyde to form a compound of (I-B)

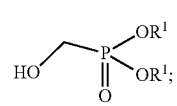

I-B (b) reacting the compound of (I-B)

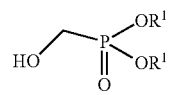
I-B and R²Cl to form a compound of (I-C)

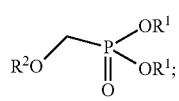
I-C (c) reacting the compound of (I-C)

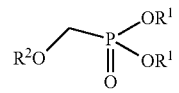
I-C with a compound of (I-E)

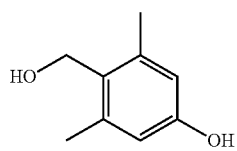
I-E to form a compound of (I-F)

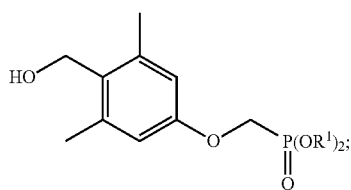
I-F (d) reacting the compound of (I-F)

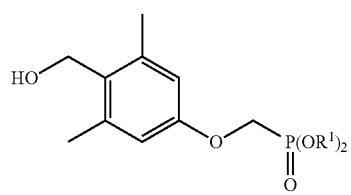
I-F with 2-benzylphenol to form a compound of (I-G)

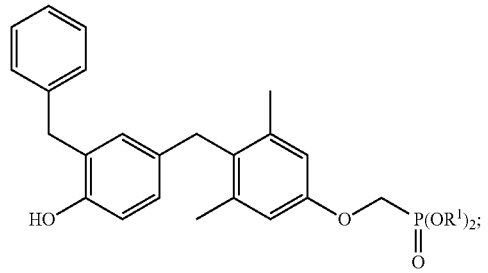
I-G (e) deprotecting the compound of formula (I-G)

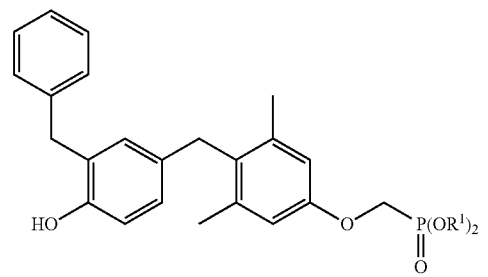
I-G to form a compound of (I-I)

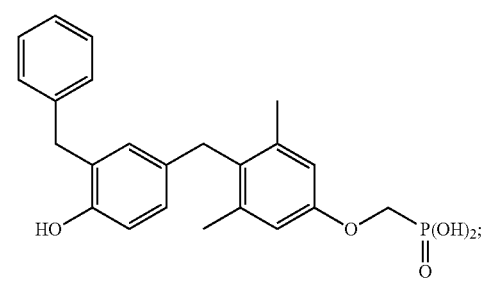
I-I wherein each $R^1$ is independently a protecting group for hydroxyl group and $R^2$ is a leaving group.

2. The method of claim 1, comprising reacting the compound of (I-I)

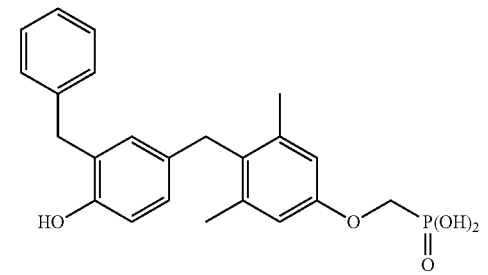
I-I with iodomethyl pivalate to form a compound of Formula I
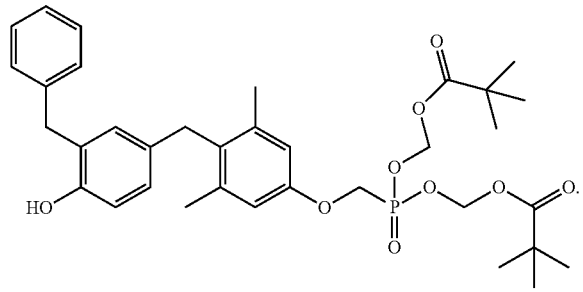
(I)
3. The method of claim 1, comprising converting chloromethyl pivalate to iodomethyl pivalate.
4. The method of claim 1, comprising reacting 3,5-dimethylphenol with formaldehyde to form the compound of compound of (I-E)
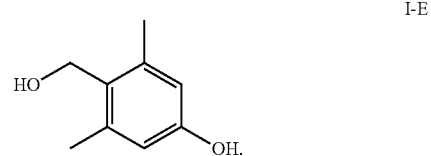
I-E
5. The method of claim 1, wherein $R^1$ is isopropyl.
6. The method of claim 1, wherein $R^2$ is tosyl.
* * * * *